United States Patent [19]

Chakrabarti et al.

[11] 4,115,568
[45] Sep. 19, 1978

[54] THIENO[3,2-b]-[1,5]BENZODIAZEPINES

[75] Inventors: Jiban Kumar Chakrabarti, Camberley; David Edward Tupper, Bracknell, both of England

[73] Assignee: Lilly Industries Limited, London, England

[21] Appl. No.: 787,197

[22] Filed: Apr. 13, 1977

Related U.S. Application Data

[62] Division of Ser. No. 633,895, Nov. 20, 1975, abandoned.

[30] Foreign Application Priority Data

Nov. 26, 1974 [GB] United Kingdom ............... 51240/74

[51] Int. Cl.² .................. A61K 31/495; A61K 31/55; C07D 495/04
[52] U.S. Cl. ..................................... 424/250; 544/146; 544/375; 260/293.57; 260/329 S; 260/329 F; 260/332.2 R; 260/332.2 A; 260/332.3 P; 260/332.5
[58] Field of Search ...................... 260/268 TR, 243.3; 424/250

[56] References Cited

U.S. PATENT DOCUMENTS

| | | | |
|---|---|---|---|
| 3,474,099 | 10/1969 | Renz et al. | 260/268 TR |
| 3,641,031 | 2/1972 | Schindler et al. | 260/268 TR |
| 3,758,479 | 9/1973 | Schmutz et al. | 260/268 TR |
| 3,761,481 | 9/1973 | Nakanishi et al. | 260/268 TR |
| 3,951,981 | 4/1976 | Safir | 260/268 TR |
| 3,985,750 | 10/1976 | Protiva et al. | 260/268 TR |

*Primary Examiner*—Jose Tovar
*Attorney, Agent, or Firm*—Kathleen R. S. Page; Everet F. Smith

[57] ABSTRACT

Thieno[1,5]benzodiazepines having useful CNS activity containing the novel tricyclic ring system:

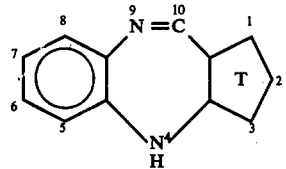

the 10-position being substituted by an amino, preferably a piperazino, group.

9 Claims, No Drawings

THIENO[3,2-b]-[1,5]BENZODIAZEPINES

This is a division of application Ser. No. 633,895, filed Nov. 20, 1975, now abandoned.

This invention relates to a novel class of compounds having useful central nervous system (hereinafter abbreviated to 'CNS') activity and/or which are useful as intermediates in preparing such active compounds. The invention also includes processes for preparing the novel compounds of the invention. Furthermore, the invention includes within its scope pharmaceutical compositions containing the active compounds and methods of treating animals, including humans, comprising administering thereto an effective dose of the compound or compounds or of pharmaceutical compositions comprising the active compound or compounds. More particularly, the invention is concerned with the hitherto unknown thieno[1,5]benzodiazepine ring system depicted below:

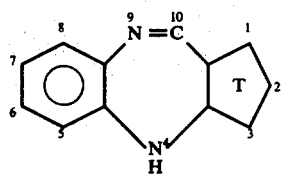

were the symbol:

signifies a thiophene ring.

In recent times, there has been intense activity in the area of pharmaceutical chemistry relating to tricyclic and benzodiazepine systems. A large number of patents have issued of which United Kingdom Pat. Nos. 980,853; 1,291,684, 1,380,242; 1,380,243; 1,380,244 and U.S. Pat. Nos. 2,893,992; 3,102,116; 3,109,843; 3,136,815; 3,474,099; 3,654,286; 3,749,786 and 3,842,082 represent only a very small proportion.

According to the present invention there is provied a novel thieno[1,5]benzodiazepine of formula (I):

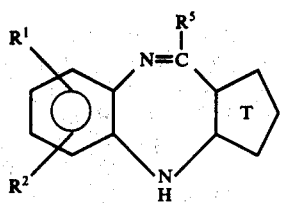

or an acid addition salt thereof, wherein $R^1$ and $R^2$ independently represent hydrogen, $C_{1-4}$ alkyl, $C_{2-4}$ alkenyl, $C_{3-6}$ cycloalkyl, halogen, $C_{1-4}$ haloalkyl, nitro, amino, $C_{2-4}$ acylamino, hydroxyl, $C_{1-4}$ alkoxy, $C_{1-4}$ alkylthio or a group of formula $—SO_2N(R^4)_2$ or $SO_2R^4$, where $R^4$ is $C_{1-4}$ alkyl; where (A) $R^5$ is a group of formula:

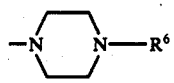

wherein $R^6$ is hydrogen, phenyl optionally substituted by halogen or $C_{1-4}$ haloalkyl, $C_{1-4}$ alkyl, $C_{3-6}$ cycloalkyl, $C_{2-4}$ alkenyl, $C_{1-4}$ alkanoyl, benzyl, $C_{1-4}$ carbalkoxy or $-(CH_2)_nOX$, where $n$ is 2 or 3 and where X is hydrogen or an ester radical; or (B) $R^5$ is a group of formula;

$$—NH—(CH_2)_n—Z$$

where $n$ is 2 or 3 and Z is

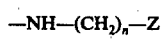 (i)

where $R^6$ is as above defined,

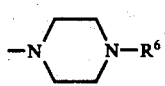 (ii)

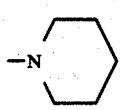 (iii)

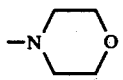 (iv)

where R" and R'" are independently hydrogen or $C_{1-4}$ alkyl, or

OH (v)

and wherein the group

represents an optionally substituted thiophene ring fused to the diazepine nucleus.

Preferably, in the compounds of formula (I) and their acid addition salts, $R^1$ and $R^2$ independently represent hydrogen, $C_{1-4}$ alkyl, halogen, $C_{1-4}$ haloalkyl, nitro, amino, $C_{1-4}$ alkoxy, $C_{1-4}$ alkylthio or a group of formula $—SO_2N(R^4)_2$ where $R^4$ is $C_{1-4}$ alkyl; and (A) $R^5$ is a group of formula: t,0042
wherein $R^6$ is hydrogen, phenyl optionally substituted by halogen, $C_{1-4}$ alkyl, $C_{1-4}$ carbalkoxy or $—(CH_2)_nOH$ where $n$ is 2 or 3; or (B) $R^5$ is a group of formula:

$$—NH—(CH_2)_n—Z$$

where $n$ is 2 or 3 and Z is

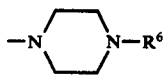 (i)

where $R^6$ is as above defined immediately above,

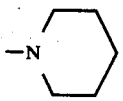 (ii)

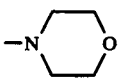 (iii)

or

 (iv)

where R" and R'" are independently hydrogen or $C_{1-4}$ alkyl.

Those skilled in the art will appreciate that the novel thieno[1,5]benzodiazepines of the invention can exist in three forms which can be represented by the following structures:

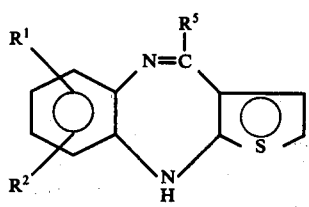 (II)

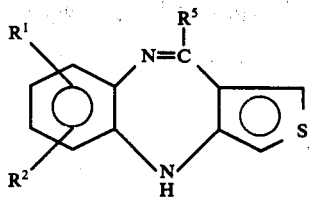 (III)

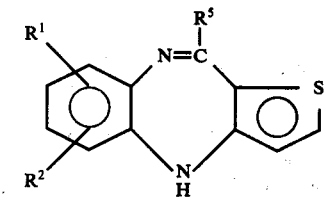 (IV)

In the above structural formulae, for ease of representation, the thiophene ring is shown as unsubstituted but it is to be understood that the thiophene ring may be substituted, for instance, by one or two groups selected from $C_1$alkyl, typically $C_{1-6}$ alkyl, $C_{2-4}$ alkenyl, $C_{1-4}$ haloalkyl, $C_{2-4}$ alkanoyl, nitro, halogen and optionally substituted phenyl. In addition, in the structures of formulae (II) and (IV), the thiophene ring may be fused to a $C_{3-8}$ cycloalkyl ring.

Preferred compounds falling within the scope of compounds defined in any of formulae (I) to (IV) above are those having one or more of the following characteristics:

(A) $R^1$ is a 6 or 7-halo substituent, such as chlorine or fluorine;
(B) $R^1$ is a 7-halo substituent such as chlorine or fluorine when $R^2$ is hydrogen;
(C) $R^1$ is a 7-fluoro substituent when $R^2$ is hydrogen;
(D) $R^2$ is hydrogen;
(E) $R^1$ or $R^2$ is trifluoromethyl;
(F) $R^1$ is a 6- or 7-trifluoromethyl substituent when $R^2$ is hydrogen;
(G) $R^1$ or $R^2$ is methylthio or methoxy;
(H) $R^1$ and $R^2$ both represent halogen atoms, for example fluorine;
(I) $R^5$ is a group of formula:

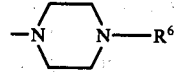

where $R^6$ is hydrogen, $C_{1-4}$ alkyl, benzyl, or $(CH_2)_nOX$;
(J) $R^5$ is a group of formula:

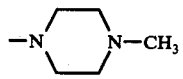

(K) the compound of formula (I) has the structure (II);
(L) the thiophene ring is substituted by a $C_{1-4}$ alkyl group, such as ethyl; (M) the thiophene ring is unsubstituted;
(N) the thiophene ring is substituted by an electron withdrawing group such as halogen, nitro, trifluoromethyl or $C_{2-4}$ alkanoyl.

A presently most preferred class of compounds is that having features (A) to (E), (J) and (L).

One particularly active compound falling within this class which may be mentioned is 2-ethyl-7-fluoro-10-(4'-methyl-1'-piperazinyl)-4H-thieno[2,3-b][1,5]benzodiazepine, both in the form of its free base and pharmaceutically acceptable salts thereof.

The term "$C_{1-4}$ alkyl" as used herein means a straight or branched chain alkyl group containing from 1 to 4 carbon atoms, i.e. methyl, ethyl, isopropyl, n-butyl, s-butyl, isobutyl, and n-butyl. The term "$C_{1-4}$ haloalkyl" means the aforesaid alkyl groups substituted by one or more halogen atoms, e.g. trifluoromethyl. The terms "$C_{1-4}$ alkoxy" and "$C_{1-4}$ alkylthio" refer to the aforementioned alkyl groups attached through an oxygen or sulphur atom respectively to the benzene or thiophene ring.

The term "$C_{2-4}$ alkenyl" refers to groups such as vinyl, allyl and butenyl.

The term "amino" as used herein indicates a group of formula $-NH_2$ and also substituted amino groups such as mono-$C_{1-4}$ alkylamino and di-$C_{1-4}$ alkylamino groups. The term $C_{2-4}$ acylamino means an amino group substituted by a $C_{2-4}$ acyl group such as acetyl. The term "$C_{1-4}$ alkanoyl" refers to groups such as formyl or acetyl.

"$C_{3-8}$ cycloalkyl" means a saturated ring having from 3 to 8 carbon atoms in the ring such as cyclopropyl, cyclobutyl, cyclopentyl, cyclohexyl, or cyclooctyl. The term "optionally substituted phenyl" as used herein means a phenyl group unsubstituted or substituted by one or more groups such as halogen, trifluoromethyl, methyl, methoxy or nitro.

Examples which may be given of the compounds of the invention are:

2-ethyl-10-(4'-methyl-1'-piperazinyl)-4H-thieno[2,3-b][1,5]benzodiazepine 7-chloro-2-ethyl-10-(4'-methyl-1'-piperazinyl)-4H-thieno[2,3-b][1,5]benzodiazepine 2-ethyl-7-fluoro-10-(4'-methyl-1'-piperazinyl)-4H-thieno[2,3-b][1,5]benzodiazepine 2-ethyl-7-trifluoromethyl-10-(4'-methyl-1'-piperazinyl)-4H-thieno[2,3-b][1,5]benzodiazepine 7-amino-2-ethyl-10-(4'-methyl-1'-piperazinyl)-4H-thieno[2,3-b][1,5]benzodiazepine 2-ethyl-7-nitro-10-(4'-methyl-1'-piperazinyl)-4H-thieno[2,3-b][1,5]benzodiazepine 2-ethyl-6-fluoro-10-(4'-methyl-1'-piperazinyl)-4H-thieno[2,3-b][1,5]benzodiazepine 2-methyl-7-N,N-dimethylsulphonamido-10-(4'-methyl-1'-piperazinyl)-4H-thieno[2,3-b][1,5]benzodiazepine 2-pentyl-7-fluoro-10-(4'-methyl-1-piperazinyl)-4H-thieno[2,3-b][1,5]benzodiazepine 2-ethyl-6-methyl-10-(4'-methyl-1'-piperazinyl)-4H-thieno[2,3-b][1,5]benzodiazepine 2-methyl-7-methoxy-10-(4'-methyl-1'-piperazinyl)-4H-thieno[2,3-b][1,5]benzodiazepine 6,7-difluoro-2-ethyl-10-(4'-methyl-1'-piperazinyl)-4H-thieno[2,3-b][1,5]benzodiazepine 2-ethyl-7-methylthio-10-(4'-methyl-1'-piperazinyl)-4H-thieno[2,3-b][1,5]benzodiazepine 6,8-difluoro-2-ethyl-10-(4'-methyl-1'-piperazinyl)-4H-thieno[2,3-b][1,5]benzodiazepine 7-fluoro-10-(4'-methyl-1'-piperazinyl)-4H-thieno[2,3-b][1,5]benzodiazepine 7-chloro-10-(4'-methyl-1'-piperazinyl)-4H-thieno[2,3-b][1,5]benzodiazepine 7-chloro-1-methyl-10-(4'-methyl-1'-piperazinyl)-4H-thieno[2,3-b][1,5]benzodiazepine 1,2-dimethyl-7-chloro-10-(4'-methyl-1'-piperazinyl)-4H-thieno[2,3-b][1,5]benzodiazepine 7-chloro-2-methyl-10-(4'-methyl-1'-piperazinyl)-4H-thieno[2,3-b][1,5]benzodiazepine 6-trifluoromethyl-2-ethyl-10-(4'-methyl-1'-piperazinyl)-4H-thieno[2,3-b][1,5]benzodiazepine 2-vinyl-7-fluoro-10-(4'-methyl-1'-piperazinyl)-4H-thieno[2,3-b][1,5]benzodiazepine 2-vinyl-7-trifluoromethyl-10-(4'-methyl-1'-piperazinyl)-4H-thieno[2,3-b][1,5]benzodiazepine 7-chloro-2-ethyl-10-(4'-methyl-1'-piperazinyl)-4H-thieno[3,2-b][1,5]benzodiazepine 2-ethyl-7-fluoro-10-(4'-methyl-1'-piperazinyl)-4H-thieno[3,2-b][1,5]benzodiazepine 2-ethyl-10-(4'-methyl-1'-piperazinyl)-4H-thieno[3,2-b][1,5]benzodiazepine 2-ethyl-7-trifluoromethyl-10-(4'-methyl-1'-piperazinyl)-4H-thieno[3,2-b][1,5]benzodiazepine 7-amino-2-ethyl-10-(4'-methyl-1'-piperazinyl)-4H-thieno[3,2-b][1,5]benzodiazepine 2-ethyl-7-nitro-10-(4'-methyl-1'-piperazinyl)-4H-thieno[3,2-b][1,5]benzodiazepine 2-ethyl-6-fluoro-10-(4'-methyl-1'-piperazinyl)-4H-thieno[3,2-b][1,5]benzodiazepine 2-methyl-7-N,N-dimethylsulphonamido-10-(4'-methyl-1'-piperazinyl)-4H-thieno[3,2-b][1,5]benzodiazepine 2-ethyl-6-methyl-10-(4'-methyl-1'-piperazinyl)-4H-thieno[3,2-b][1,5]benzodiazepine 2-methyl-7-methoxy-10-(4'-methyl-1'-piperazinyl)-4H-thieno[3,2-b][1,5]benzodiazepine 6,7-difluoro-2-ethyl-10-(4'-methyl-1'-piperazinyl)-4H-thieno[3,2-b][1,5]benzodiazepine 2-ethyl-7-methylthio-10-(4'-methyl-1'-piperazinyl)-4H-thieno[3,2-b][1,5]benzodiazepine 6,8-difluoro-2-ethyl-10-(4'-methyl-1'-piperazinyl)-4H-thieno[3,2-b][1,5]benzodiazepine 7-fluoro-10-(4'-methyl-1'-piperazinyl)-4H-thieno[3,2-b][1,5]benzodiazepine 7-chloro-10-(4'-methyl-1'-piperazinyl)-4H-thieno[3,2-b][1,5]benzodiazepine 2,3-dimethyl-7-chloro-10-(4'-methyl-1'-piperazinyl)-4H-thieno[3,2-b][1,5]benzodiazepine 7-chloro-2-methyl-10-(4'-methyl-1'-piperazinyl)-4H-thieno[3,2-b][1,5]benzodiazepine 9-fluoro-12-(4'-methyl-1'-piperazinyl)-6H-1,2,3,4-tetrahydrobenzo-[b]thieno[2,3-b][1,5]benzodiazepine 2-ethyl-7-fluoro-10-[4'-(2-hydroxyethyl)-1-piperazinyl]-4H-thieno[2,3-b][1,5]benzodiazepine 2-ethyl-7-fluoro-10-[4'-(3-hydroxypropyl)-1-piperazinyl]-4H-thieno[2,3-b][1,5]benzodiazepine 2-octyl-7-fluoro-10-(4'-methyl-1-piperazinyl)-4H-thieno[2,3-b][1,5]benzodiazepine 2-ethyl-7-fluoro-10-(1'-piperazinyl)-4H-thieno[2,3-b][1,5]benzodiazepine 2-ethyl-7-fluoro-10-[N-(N',N'-dimethylaminoethyl)amino]-4H-thieno[2,3-b][1,5]benzodiazepine 2-ethyl-7-fluoro-10-(2'-N-piperidinoethyl)amino-4H-thieno[2,3-b][1,5]benzodiazepine 2-ethyl-7-fluoro-10-(4'-allyl-1'-piperazinyl)-4H-thieno[2,3-b][1,5]benzodiazepine 2-ethyl-7-chloro-10-[3'-(4-phenyl-1-piperazinyl)propyl]amino-4H-thieno[2,3-b][1,5]benzodiazepine 2-ethyl-7-chloro-10-[3'-(4-hydroxyethyl-1-piperazinyl)propyl]amino-4H-thieno[2,3-b][1,5]benzodiazepine 3-methyl-10-(4'-methyl-1'-piperazinyl)-4H-thieno[3,4-b][1,5]benzodiazepine 3-methyl-7-chloro-10-(4'-methyl-1'-piperazinyl)-4H-thieno[3,4-b][1,5]benzodiazepine 7-fluoro-10-(4'-acetyl-1'-piperazinyl)-4H-thieno[3,4-b][1,5]benzodiazepine 7-trifluoromethyl-10-(4'-methyl-1'-piperazinyl)-4H-thieno[3,4-b][1,5]benzodiazepine 7-amino-10-(4'-methyl-1'-piperazinyl)-4H-thieno[3,4-b][1,5]benzodiazepine 7-acetylamino-10-(4'-methyl-1'-piperazinyl)-4H-thieno[2,3-b][1,5]benzodiazepine 7-methylamino-10-(4'-methyl-1'-piperazinyl)-4H-thieno[2,3-b][1,5]benzodiazepine 7-dimethylamino-10-(4'-methyl-1'-piperazinyl)-4H-thieno[2,3-b][1,5]benzodiazepine 7-nitro-10-(4'-methyl-1'-piperazinyl)-4H-thieno[3,4-b][1,5]benzodiazepine 6-fluoro-10-(4'-methyl-1'-piperazinyl)-4H-thieno[3,4-b][1,5]benzodiazepine 3-methyl-7-N,N-dimethylsulphonamido-10-(4'-methyl-1'-piperazinyl)-4H-thieno[3,4-b][1,5]benzodiazepine 2-ethyl-7-hydroxy-10-(4'-methyl-1'-piperazinyl)-4H-thieno[2,3-b][1,5]benzodiazepine 6-methyl-10-(4'-methyl-1'-piperazinyl)-4H-thieno[3,4-b][1,5]benzodiazepine 3-methyl-7-methoxy-10-(4'-methyl-1'-piperazinyl)-4H-thieno[3,4-b][1,5]benzodiazepine 6,7-difluoro-10-(4'-methyl-1'-piperazinyl)-4H-thieno[3,4-b][1,5]benzodiazepine 7-methylthio-10-(4'-methyl-1'-piperazinyl)-4H-thieno[3,4-b][1,5]benzodiazepine 6,8-difluoro-10-(4'-methyl-1'-piperazinyl)-4H-thieno[3,4-b][1,5]benzodiazepine 7-chloro-10-(4'-methyl-1'-piperazinyl)-4H-thieno[3,4-b][1,5]benzodiazepine 7-fluoro-10-(4'-methyl-1'-piperazinyl)-4H-thieno[3,4-b][1,5]benzodiazepine 2-ethyl-7-fluoro-10-[4'-(2-hydroxyethyl)-1'-piperazinyl]-4H-thieno[3,2-b][1,5]benzodiazepine As indicated above, the novel thieno[1,5]benzodiazepines of the invention are useful both in their free base and acid addition salt forms. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic maleic, hydroxymaleic, fumaric, malic, tartaric, citric, salicylic, o-acetoxybenzoic, nicotinic or isonicotinic acid, or organic sulphonic acids for example methane sulphonic, ethane sulphonic, 2-hydroxyethane sulphonic, toluene-p-sulphonic, or naphthalene-2-sulphonic acid. Apart from pharmaceutically acceptable acid addition salts, other salts are also included within the scope of acid addition salts such as, for example, those with picric or oxalic acid; they may serve as intermediates in the purification of the compounds or in the preparation of other, for example, pharmaceutically acceptable, acid addition salts, or are useful for identification, characterization or purification of the bases.

According to a second aspect of the invention there is provided a method of preparing a compound of formula (I) which comprises:

(a) reacting an amine of formula $R^5H$ with a compound of formula (V):

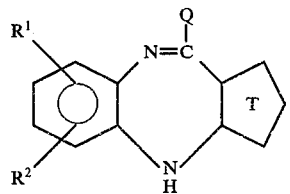

where $R^1$, $R^2$ and $R^5$ are as defined above and wherein

represents an optionally substituted fused thiophene ring as before, and wherein Q represents a radical capable of being split off with the hydrogen atom of the amine $R^5H$, followed, if desired, in the case where $R^5$ is

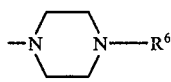

and $R^6$ is $C_{1-4}$ carbalkoxy by hydrolysis to the amine in which $R^6$ is hydrogen; or (b) reacting a compound of formula (VI):

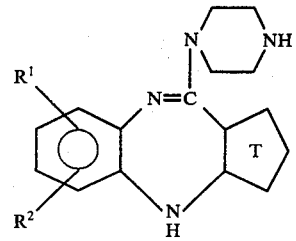

with an alkylating agent of formula $R^6X$, where $R^6$ is as above defined with the exception of hydrogen and phenyl, and where X is a reactive atom.

It should be noted that both processes (a) and (b) above are "analogy processes" of a reaction type previously described in the literature (see, for example, United Kingdom patent specification No. 1,216,523 for the reaction (a) and almost any standard treatise in the art for references to alkylation). Thus, once the nature of the starting materials and final products is understood, those skilled in the art will appreciate the identity of suitable Q and X radicals, as well as appropriate reaction conditions.

However, it may be mentioned that the radical Q may be hydroxyl or thiol, an alkoxy or alkylthio group containing 1 to 4 carbon atoms, e.g. the methoxy or methylthio group, an aryloxy, aralkylthio or arylthio group which may be activated as a leaving group by substituents thereon conveniently in the aryl moiety thereof, e.g. the p-nitrobenzylthio group, an alkyl- or arylsulpheno group, preferably activated as a leaving group by substituents on the sulphur atom and the hydrocarbon moiety thereof, e.g. a tosyl group, a halogen atom, conveniently a chlorine atom, an amino group or a mono- or dialkyl-substituted amino group, the or each alkyl substituent thereof containing 1 to 4 carbon atoms.

Preferably, Q is hydroxyl, thiol, $C_{1-4}$ alkoxy, $C_{1-4}$ alkylthio, halogen or $NH_2$.

Most preferably, Q is hydroxyl or thiol, when the intermediates of formula (V) exist predominantly in their amide and thioamide forms:

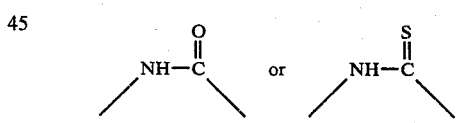

When Q is hydroxyl, and thus the compound of formula (V) is an amide, reaction (a) can be accomplished in the presence of titanium tetrachloride. This last named reagent has the ability to react with the amine of formula $R^5H$ to form a metal amine complex. Other metal chlorides such as those of zirconium, hafnium or vanadium also possess this property. The reaction is preferably carried out in the presence of an acid binding agent such as a tertiary amine, for example, triethylamine.

Alternatively, the reaction can be carried out using excess of the amine of formula $R^5H$ to act as acid-binding agent.

Any suitable organic solvent such as toluene or chlorobenzene can be used although it has been found that the use of anisole is particularly desirable at least as a co-solvent, in view of its ability to form a soluble complex with $TiCl_4$.

If desired, elevated temperatures (up to 140° C.) can be used to expedite the reaction. A preferred temperature range for carrying out the reaction lies in the range 50° to 100° C.

The amidines of formula (V), i.e. where Q is NH$_2$, can be similarly condensed with the amine of formula R$^5$H, although the yield from this reaction may be rather low. In fact, it is generally preferable to convert the amidine into the corresponding amide by alkaline hydrolysis and use the thus formed amide for the condensation reaction.

Thioamides of formula (V), Q is SH, can be prepared by treating a solution of the corresponding amide in an anhydrous basic solvent such as dry pyridine, with phosphorous pentasulphide. Similarly, the amides may be converted to iminothioethers, iminoethers or iminohalides, or other derivatives containing active Q radicals as specified above, by treatment with conventional reagents such as, for an iminochloride, phosphorous pentachloride. Such derivatives derived from the amides tend to be more reactive towards the amine R$^5$H and can usually be reacted with that entity without the necessity for the presence of TiCl$_4$.

Compounds of formula (VI) can be alkylated by dissolving the amine in a suitable inert polar solvent such as ethanol, adding the alkylating agent to the solution thus formed and refluxing in the presence of base. X can be any suitable reactive atom such as chlorine, bromine or iodine or a reactive group such as tosyl or mesyl.

Compounds of formula (I) in which R$^5$ represents:

are preferably prepared by hydrolysis of the corresponding C$_{1-4}$ carbalkoxy derivative.

Electrophilic substitution reactions on the aromatic nucleus can, if desired, be carried out on compounds of formula (I) or (V) in conventional manner to produce derivatives bearing electon-withdrawing groups on the thiophene ring. For instance, acetylation of an amide of formula (V) can be effected using acetyl chloride/SnCl$_4$. This amide may also be halogenated using, for example, N-chlorosuccinimide to give the corresponding chlorinated derivative. Products of formula (I) in which R$^1$ or R$^2$ are NH$_2$ may be acylated or alkylated in conventional manner to form the corresponding N-acyl and N-alkylamino derivatives. N-Hydroxyalkylpiperazines, i.e. R$^6$ is —(CH$_2$)$_n$OH, can be esterified using acid chlorides of fatty acids to give corresponding esters, such as decanoates or enanthates.

The compounds of formula (I) produced by the foregoing process may be isolated per se or may be converted to their corresponding acid addition salts using conventional methods.

The amides of formula (V) can be formed by a novel process which involves the intramolecular ring-closure of an amino ester of formula (VII):

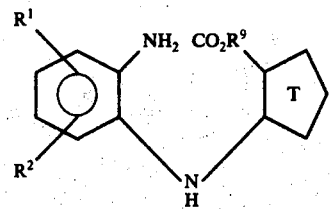

where R$^9$ is C$_{1-4}$ alkyl, e.g. ethyl, and R$^1$, R$^2$ and

are as defined previously. This reaction can be accomplished using dimsyl sodium in a suitable solvent, preferably dimethyl sulphoxide.

Alternatively, amides of formula (V) can be produced by intramolecular ring-closure of an amino acid of formula (VIII):

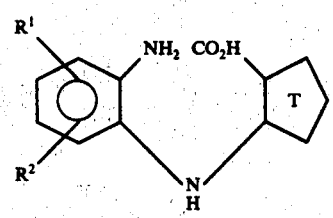

using dicyclohexylcarbodiimide (D.C.C.) with a suitable solvent such as tetrahydrofuran. The amino acids can be obtained from the esters by basic hydrolysis using, e.g. NaOH/EtOH.

As mentioned previously, a convenient way of preparing amides of formula (V) involves the following reaction:

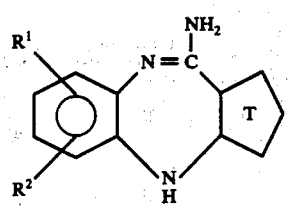

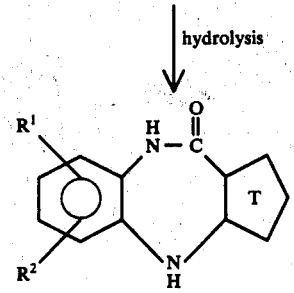

The hydrolysis may be carried out using alkaline hydrolytic conditions, for example, K$_2$CO$_3$/H$_2$O/EtOH.

One convenient method of preparing amidines of formula (IX) is illustrated below:

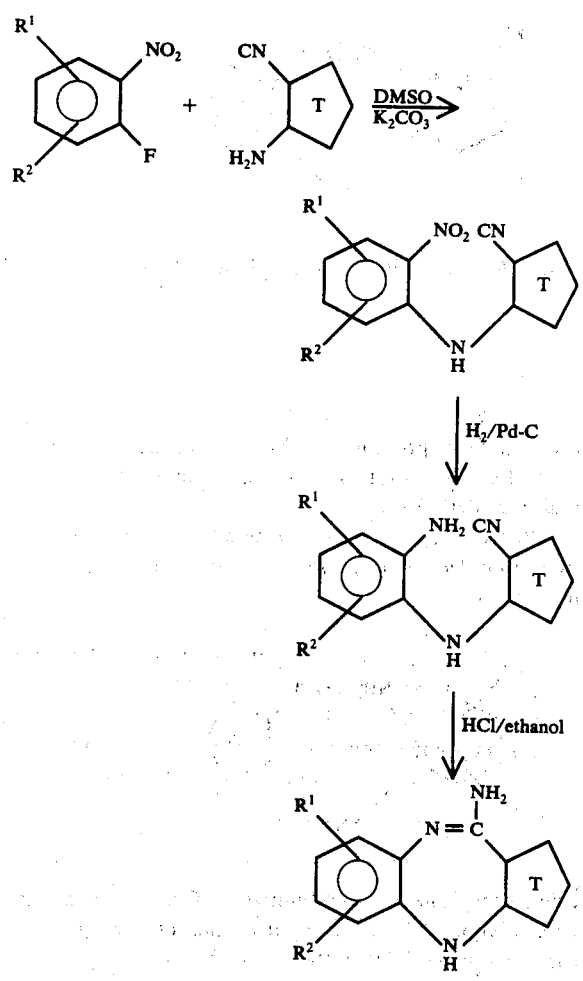

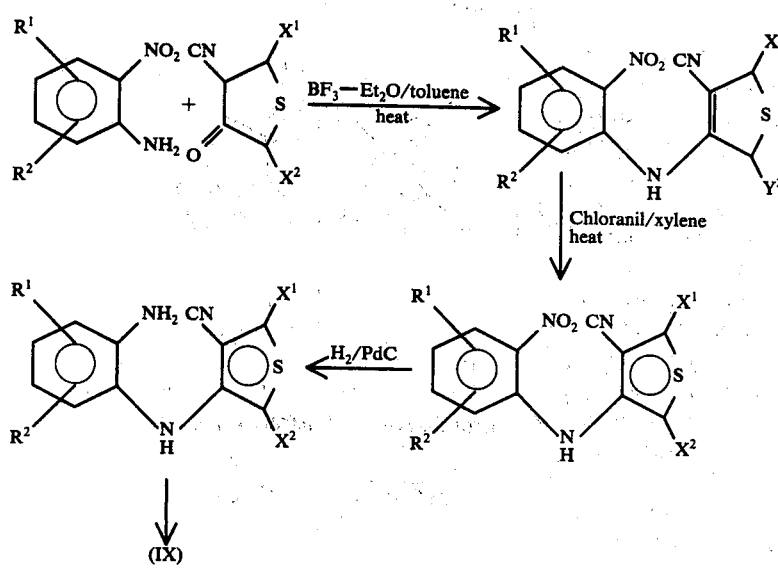

Alternatively, amidines in the [3,4-b]system may be prepared by the following reaction sequence:

where $X^1$ and $X^2$ indicate optional substituents on the thiophene ring. As can be seen, the above reaction involves an "aromatisation" reaction using chloranil and xylene.

Alternatively, the above condensation reaction may be effected using o-phenylenediamines in place of the nitroanilines.

The esters of formula (VII) are novel compounds which can be prepared by condensation of a thiophene compound of formula:

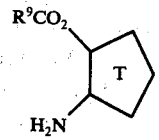

where $R^9$ is as above defined, with an ortho-fluoronitrobenzene of formula:

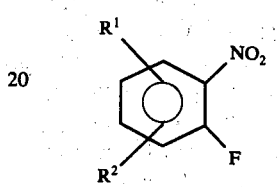

in the presence of an n-butyl lithium derivative, or in the presence of a base such as sodium hydride, sodium amide, triethylamine, or $K_2CO_3$ in dimethyl sulphoxide, to form a nitro ester of formula:

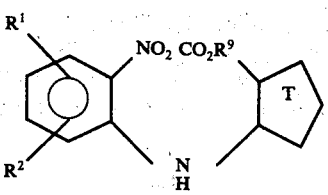

which can then be reduced to the amino ester of formula (VII) catalytically, for instance using hydrogen over palladium on charcoal, or chemically using Zn/NH$_4$Cl, ammonium polysulphide or Fe/HCl.

For example, 4H-thieno[2,3-b][1,5]benzodiazepin-10-ones can be prepared by the following illustrative reaction scheme:

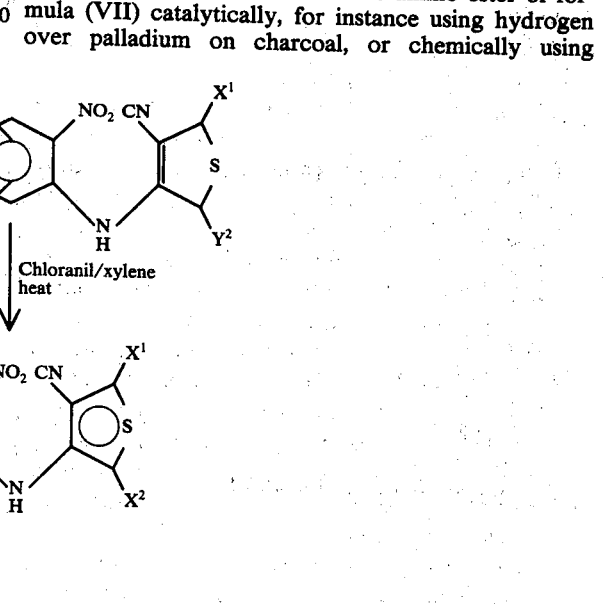

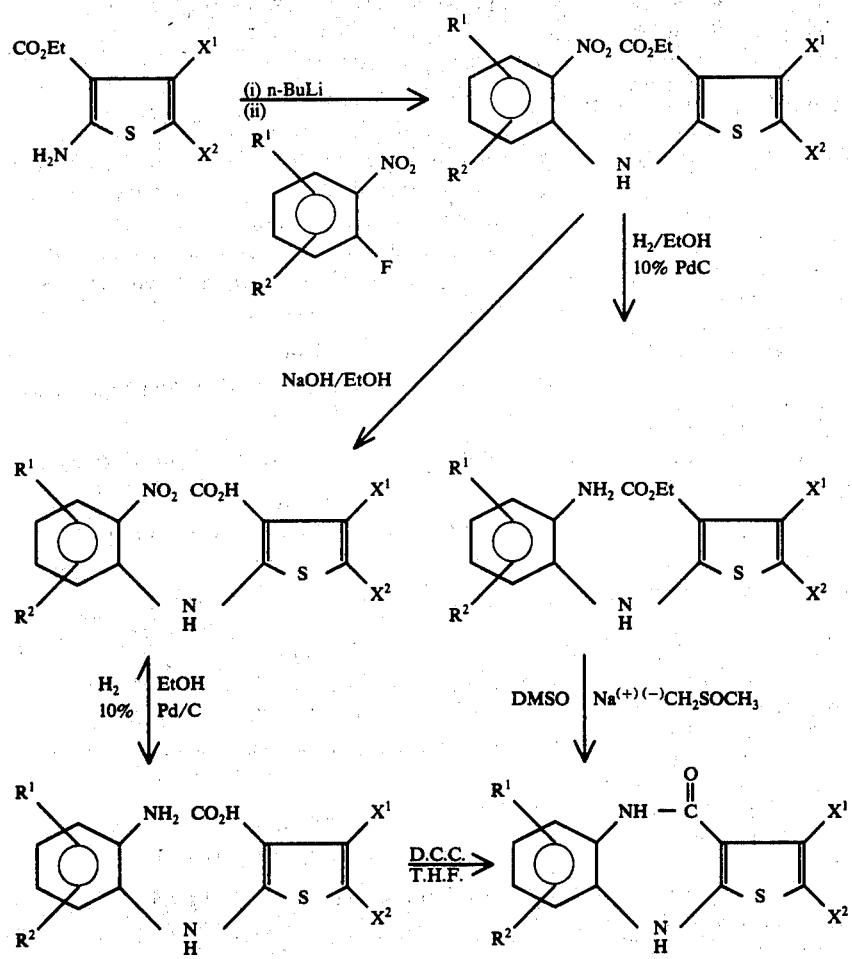

Other thieno[1,5]benzodiazepin-10-ones can be similarly prepared via the amino ester route outlined above.

The thiophene starting materials used in the processes of the invention are either known compounds, see, for example, Chem. Berichte, 99, 94–100, (1966) J. Am. Chem. Soc., 68 2232 (1946) and Dutch Patent Application No. 66 04742, or can be prepared by conventional techniques from known compounds. The o-fluoro nitrobenzene intermediates are either commercially available or can be simply prepared from commercially available substances.

It will be understood the scope of the invention extends not only to an overall process for preparing the novel compounds of the invention as described hereinbefore but also to the individual synthetic steps as herein described, and combinations of two or more of such synthetic steps. Further, the intermediates of formula (V), (VII), (VIII), (IX) and (X) are all novel compounds and are provided in further aspects of the invention.

As stated previously, the compounds of the invention have useful central nervous system activity. This activity has been demonstrated in extensive testing in animal models using well-established procedures, such as the production of catalepsy, block of conditioned avoidance response and reversal of amphetamine-induced stereotyped behaviour in rats. Specifically, the compounds of formula (I) and acid addition salts thereof, are potent centrally acting compounds with neuroleptic, sedative or relaxant or anti-emetic properties. These properties, coupled with their high therapeutic index, render them useful in the treatment of mild anxiety states and certain kinds of psychotic conditions such as schizophrenia and acute mania.

The compounds of this invention are effective over a wide dosage range, the actual dose administered being dependent on such factors as the particular compound being used, the condition being treated and the type and size of mammal being treated. However, the dosage required will normally fall within the range of 0.1 to 20 mg./Kg. per day, for example in the treatment of adult humans dosages of from 0.1 to 10 mg./Kg. may be used.

The compounds and salts of the present invention will normally be administered orally or by injection and, for this purpose, said compounds and salts will usually be utilised in the form of a pharmaceutical composition. Such compositions are prepared in a manner well known in the pharmaceutical art and normally comprise at least one active compound or pharmaceutically-acceptable salt of the invention associated with a pharmaceutically-acceptable carrier therefor. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or mineral oil. The compositions of the invention may, as is well-known in the art, be formulated so as to provide quick, sustained or delayed release of the active ingredient after administration to the patient.

Depending on the route of administration, the foregoing compositions may be formulated as tablets, capsules or suspensions for oral use and injection solutions for parenteral use. Preferably the compositions are formulated in a dosage unit form, each dosage containing from 1 to 200 mg. more usually 5 to 100 mg., of the active ingredient.

The following preparation and Examples will further illustrate the invention. In cases where melting points are not given, support for the structure of final (title) products was usually obtained by thin-layer chromatography and/or spectral data.

PREPARATION 1

α'-Carboxymethyl-β'-carboxyethyl-α-ethylethylmethylsulphide

Ethyl pent-3-enoate (12.6 g, 0.1 mol) *J. Org. Chem.* 12, 138–154, was added dropwise to a solution of methyl thioglycolate (10.6 g, 0.1 mol) and piperidine (0.1 ml) which were stirred together in a three-necked 100 ml flask equipped with a dropping funnel, thermometer and condenser. The temperature of the reaction was kept between 40°–50° C., piperidine (0.6 ml) being added in 0.05 ml amounts over a period of 45 minutes. After the addition of pentenoate, the reaction was maintained at 50° C. for 10 minutes. The reaction mixture was then cooled, washed with water, dried over MgSO$_4$, filtered and the filter pad washed with ether. The combined filtrate was evaporated to dryness and the title compound obtained as a yellow liquid.

EXAMPLE 1

(a) Ethyl 5-ethyl-2-(2-nitroanilino)-thiophene-3-carboxylate

Ethyl 2-amino-5-ethyl-thiophene-3-carboxylate (Ber. 99, 94-100) (40 g, 0.2 mol) in dry tetrahydrofuran (150 ml) was stirred under nitrogen and cooled to −40° C. n-Butyl lithium (125 ml of 10.2% w/v solution in hexane, 0.2 mol) was added keeping the temperature below −30° C. The mixture was then stirred at −30° C. for a further 15 minutes. This solution was blown by nitrogen through an inverted "U" tube into a solution of o-fluoro-nitrobenzene (28 g, 0.2 mol) in dry tetrahydrofuran (100 ml) maintained at 15°–30° C. The mixture was stirred overnight. The resulting ink-blue solution was poured into three volumes of ice water, extracted with ether (3 × 500 ml), washed with water (2 × 500 ml), dried and then evaporated to dryness. The deep red oil was dissolved in ethanol (200 ml) and chilled overnight. Crystals of the title compound were filtered off and dried in vacuo at 50° C.

Recrystallisation from ethanol gave pure product having a m.p. of 66°–68° C.

(b) Ethyl 5-ethyl-2-(4-fluoro-2-nitroanilino)-thiophene-3-carboxylate

The title compound was similarly prepared but using 2,5-difluoro-nitrobenzene in place of the o-fluoronitrobenzene used in Example 1(a) above, m.p. 90° C. (after recrystallisation from ethanol).

Anal.Calc. for C$_{15}$H$_{15}$FN$_2$O$_4$S: C: 53.24; H: 4.45; N: 8.28; F: 5.61; S: 9.47%.

Found C: 53.45; H: 4.75; N: 8.15; F: 5.71;

Similarly, using the procedure described in Example 1(a), the following compounds were prepared. In each case, the nitrobenzene used in place of the o-nitrobenzene of Example 1(a) is given, as is the melting point of the *title* compound, together with recrystallisation solvent—indicated in parenthesis.

(c) Ethyl 2-(3,5-difluoro-2-nitroanilino)-5-ethyl-thiophene-3-carboxylate 2,4,6-Trifluoro-nitrobenzene, m.p. 74°–75° C. (EtOH).

(d) Ethyl 5-ethyl-2-(5-fluoro-2-nitroanilino)-thiophene-3-carboxylate 2,4-Difluoro-nitrobenzene, m.p. 87°–88° C. (EtOH).

(e) Ethyl 2-(4-chloro-2-nitroanilino)-5-ethyl-thiophene-3-carboxylate

5-Chloro-2-fluoro-nitrobenzene, m.p. 75°–76.5° C. (EtOH).

(f) Ethyl 2-(2,4-dinitroanilino)-5-ethyl-thiophene-3-carboxylate 2,4-Dinitro-fluorobenzene, 148° C. (EtOH).

(g) Ethyl 2-(4-fluoro-2-nitroanilino)-4,5,6,7-tetrahydrobenzo[b]-thiophene-3-carboxylate The title compound was similarly prepared using the process of Example 1(a) but using as starting materials 2,5-difluoro-nitrobenzene and ethyl 2-amino-4,5,6,7-tetrahydrobenzo[b]thiophene-3-carboxylate, m.p. 140°–142° C. (EtOH).

(h) Ethyl 2-(4,5-difluoro-2-nitroanilino)-5-ethyl-thiophene-3-carboxylate 2,4,5-Trifluoro-nitrobenzene, m.p. 105° C. (EtOH).

(i) Methyl 3-(2-nitroanilino)-thiophene-2-carboxylate

The title compound was prepared using the process of Example 1(a) but with 2-fluoro-nitrobenzene and methyl 3-aminothiophene-2-carboxylate (U.K. Pat. No. 837,086) as starting materials, m.p. 184° C., (toluene/MeOH, 2:1).

(j) Methyl 3-(4-fluoro-2-nitroanilino)-thiophene-2-carboxylate

The title compound was prepared using the process of Example 1(a) but with 2,5-difluoronitrobenzene and methyl 3-aminothiophene-2-carboxylate as starting materials, m.p. 172°–175° C. (benzene).

Similarly prepared were:

(k) Ethyl 5-i-propyl-2-(4-fluoro-2-nitroanilino)-thiophene-3-carboxylate (l) Ethyl 5-n-hexyl-2-(4-fluoro-2-nitroanilino)-thiophene-3-carboxylate (m) Ethyl 4-methyl-2-(4-fluoro-2-nitroanilino)-thiophene-3-carboxylate (n) Ethyl 4-methyl-5-ethyl-2-(4-fluoro-2-nitroanilino)-thiophene-3-carboxylate

EXAMPLE 2

(a) Ethyl 5-ethyl-2-(2-nitroanilino)-thiophene-3-carboxylate o-Fluoronitrobenzene (56.4 g, 0.4 mol) and ethyl 2-amino-5-ethylthiophene-3-carboxylate (100 g, 0.5 mol) were dissolved in dry dimethylsulphoxide (320 ml). The stirred solution, under nitrogen, was heated in an oil bath. When the internal temperature reached 60° C., potassium carbonate (55 g, 0.4 mol) was added and the mixture stirred at 100° C. until GLC. indicated that all the o-fluoronitrobenzene had been consumed (6.5 hours). The mixture was then poured onto ice-water, acidified with concentrated hydrochloric acid and extracted with methylene chloride. The combined extracts were washed with water, dried (MgSO$_4$) and the solvent evaporated to give a red semi-solid which was recrystallised from ethanol to give the title product as a solid (m.p. 66°-68° C.).

The following compounds were similarly prepared using the process of Example 2(a). In each case, the melting point of the title compound, the recrystallisation solvent - indicated in parentheses - and the starting materials (when different from those of Example 2(a)) are given.

(b) Ethyl 2-(4-chloro-2-nitroanilino)-5-ethyl-thiophene-3-carboxylate

5-Chloro-2-fluoro-nitrobenzene, m.p. 75°-76° C. (EtOH).

(c) Ethyl 2-(2,4-dinitroanilino)-5-ethyl-thiophene-3-carboxylate 2,4-Dinitro-fluorobenzene, m.p. 146°-148° C. (EtOH).

(d) Ethyl 5-ethyl-2-(2-nitro-4-trifluoromethylanilino)-thiophene-3-carboxylate

4-Fluoro-3-nitrobenzotrifluoride, m.p. 102° C. (EtOH).

(e) Ethyl 5-ethyl-2-(5-methyl-2-nitroanilino)-thiophene-3-carboxylate

3-Fluoro-4-nitrotoluene, m.p. 55°-57° C. (EtOH).

(f) Ethyl 2-(4-difluoromethyl-2-nitroanilino)-5-ethyl-thiophene-3-carboxylate

5-Difluoromethyl-2-fluoro-nitrobenzene, m.p. 88°-90° C. (EtOH).

(g) Methyl 2-(4-N,N-dimethylsulphonamido-2-nitroanilino)-5-ethyl-thiophene-3-carboxylate 5-N,N-Dimethylsulphonamido-2-fluoro-nitrobenzene and methyl 2-amino-5-ethyl-thiophene-3-carboxylate, m.p. 166°-168° C. (EtOH).

(h) Methyl 5-ethyl-2-(4-methoxy-2-nitroanilino)-thiophene-3-carboxylate

2-Fluoro-5-methoxy-nitrobenzene and methyl 2-amino-5-ethyl-thiophene-3-carboxylate, m.p. 125°-127° C. (EtOH).

(i) Ethyl 2-(4-fluoro-2-nitroanilino)-thiophene-3-carboxylate 2,5-Difluoro-nitrobenzene and ethyl 2-amino-thiophene-3-carboxylate, m.p. 125° C. (EtOH).

(j) Ethyl 5-ethyl-2-(4-methylthio-2-nitroanilino)-thiophene-3-carboxylate

4-Fluoro-3-nitro-thioanisole and ethyl 2-amino-5-ethyl-thiophene-3-carboxylate.

(k) Ethyl 2-(2-chloro-6-nitroanilino)-5-ethyl-thiophene-3-carboxylate

Ethyl 2-amino-5-ethyl-thiophene-3-carboxylate and 3-chloro-2-fluoronitrobenzene, m.p. 67°-70° C. (EtOH).

(l) Ethyl 5-ethyl-2-(2-trifluoromethyl-6-nitroanilino)-thiophene-3-carboxylate

Ethyl 2-amino-5-ethylthiophene-3-carboxylate and 2-fluoro-3-trifluoromethylnitrobenzene, m.p. 72°-73° C. (EtOH).

(m) Methyl 3-(4-chloro-2-nitroanilino)-thiophene-2-carboxylate

5-Chloro-2-fluoro-nitrobenzene and methyl 3-amino-thiophene-2-carboxylate, m.p. 207°-208° C. (EtOAc/Hexane).

(n) Methyl 5-methyl-2-(2-nitro-4-fluoroanilino)-thiophene-3-carboxylate

Methyl 2-amino-5-methyl-thiophene-3-carboxylate and 2,5-difluoronitrobenzene, m.p. 149°-151° C. (EtOH).

(o) Ethyl 2-(4-bromo-2-nitroanilino)-5-ethyl-thiophene-3-carboxylate

Ethyl 2-amino-5-ethyl-thiophene-3-carboxylate and 5-bromo-2-fluoronitrobenzene, m.p. 76°-78° C. EtOH).

(p) Methyl 2-(4-fluoro-2-nitroanilino)-5-phenyl-thiophene-3-carboxylate

Methyl 2-amino-5-phenyl-thiophene-3-carboxylate and 2,5-difluoronitrobenzene, m.p. 150° C. (CH$_2$Cl$_2$).

(q) 5-Ethyl-2-(2-nitroanilino)-thiophene-3-carboxylic acid

Ethyl 5-ethyl-2-(2-nitroanilino)-thiophene-3-carboxylate (6.0 g) dissolved in ethanol (100 ml) and water (50 ml) and heated to 60° C. with stirring. Sodium hydroxide (5N, 50 ml) was then added and the temperature maintained for 16 hours. The reaction mixture was cooled and diluted with water (500 ml), and solid title product filtered off, m.p. 189°–191° C. (EtOAc).

(r) 5-Ethyl-2-(4-fluoro-2-nitroanilino)-thiophene-3-carboxylic acid

The title compound was similarly prepared from ethyl 5-ethyl-2-(4-fluoro-2-nitroanilino)-thiophene-3-carboxylate but using a reaction temperature of 25° C., m.p. 198°–200° C. (EtOAc).

(s) Methyl 5-Ethyl-3-(4-fluoro-2-nitroanilino)-thiophene-2-carboxylate

EXAMPLE 3

(a) Methyl 3-(4-fluoro-2-nitroanilino)-thiophene-4-carboxylate

3-Carboxymethyl-4-aminothiophene hydrochloride *J.A.C.S.* 68, 2232 (1946) (48.5 g, 0.25 mol) was dissolved in a minimum of water and shaken in the presence of saturated sodium bicarbonate solution and ether. The ether extract was dried with MgSO$_4$, filtered and evaporated to an oil, dissolved in dimethylformamide (DMF), 2-methoxyethanol, or dimethylsulphoxide (DMSO) (anhydrous), preferably the latter (100 ml). To this stirred solution at 100° C., under nitrogen, was added 2,5-difluoronitrobenzene (40 g, 0.25 mol) and triethylamine (35 ml), the reaction was kept at these conditions for an hour (under reflux) and more triethylamine (35 ml) added. The reaction was then heated, with stirring under nitrogen for a further 40 hours.

The chilled mixture was poured into saturated brine (1½ liters) with stirring, in the presence of ethyl acetate, the two-phase mixture was filtered. The organic phase was run off, washed with brine, dried with MgSO$_4$, filtered and evaporated to a brown gum. This gum was dissolved in a minimum of ethyl acetate and vacuum-filtered through a pad of "Florisil" (trade mark) contained in a sintered funnel, the pad was washed with ethyl acetate until all the product had been removed, the filtrates bulked, evaporated to an oil, dissolved in cold ethanol (250 ml) and left at 0° C. for 24 hours. The red-orange crystalline product occasionally contained traces of brown tar, but it was found that this could be removed by adding a little ethyl acetate and triturating. The crystals so obtained were filtered, washed with ethanol, 40°–60° C. petrol, and then dried under vacuo to give the title compound as a solid product, m.p. 164° C.

(b) Methyl 3-(2-nitro-4-trifluoromethylanilino)-thiophene-4-carboxylate

The title compound was similarly prepared using the process described in Example 3(a) above, m.p. 175° C. (EtOH).

(c) 2-(4-Fluoro-2-nitroanilino)-4,5,6,7-tetrahydrobenzo[b]-thiophene-3-nitrile 2-Amino-4,5,6,7-tetrahydrobenzo[b]thiophene-3-nitrile (3.6 g, 0.02 mol) and 2,5-difluoronitrobenzene (3.2 g, 0.02 mol) in dry DMSO (20 ml) was stirred and heated on an oil bath. When the internal temperature reached 60° C, potassium carbonate (2.76 g, 0.02 mol) was added and the mixture then stirred at 100° C. for 5 hours. The reaction mixture was poured onto ice-water, acidified and extracted with methylene chloride. The combined extracts were washed with water, dried (MgSO$_4$) and the solvent removed in vacuo, m.p. 137°–139° C. (EtOAc).

Similarly, the following compounds were prepared using 2-amino-5-ethyl-thiophene-3-nitrile.

(d) 5-Ethyl-2-(4-fluoro-2-nitroanilino)-thiophene-3-nitrile

(e) 5-Ethyl-2-(4-methoxy-2-nitroanilino)-thiophene-3-nitrile

(f) 5-Ethyl-2-(4-methylthio-2-nitroanilino)-thiophene-3-nitrile

(g) 5-Ethyl-2-(2-nitro-4-trifluoromethylanilino)-thiophene-3-nitrile

EXAMPLE 4

(a) 3-(4-Chloro-2-nitroanilino)-2,5-dihydrothiophene-4-nitrile

3-Cyanotetrahydrothiophen-4-one (Dutch patent application No. 66,04742) (38.1 g, 0.25 mol) and 4-chloro-2-nitroaniline (51.8 g, 0.28 mol) were dissolved in refluxing toluene (~200 ml) in a three-necked flask (500 ml) fitted with a Dean and Stark apparatus. A few drops of boron trifluoride etherate were added and the reaction was left to reflux for 4 hours, the water formed being tapped off.

The reaction mixture was left to cool whereupon a brown solid precipitated and was filtered off. The solid was recrystallised from absolute ethanol using activated charcoal as a decolouriser, and the orange crystalline solid which was obtained was filtered, washed with ethanol and then dried at 50° C. under vacuum. The dried solid so obtained was the title compound which had a melting point of 154°–155° C.

(b) 3-(4-Methylthio-2-nitroanilino)-2,5-dihydrothiophene-4-nitrile

The title compound was obtained using a similar procedure to that outlined in Example 4(a) above, m.p. 141°–142° C. (EtOH).

(c) 4-(4-Fluoro-2-nitroanilino)-2-ethyl-2,5-dihydrothiophene-3-nitrile

EXAMPLE 5

(a) 3-(4-Chloro-2-nitroanilino)-thiophene-4-nitrile 3-(4-Chloro-2-nitroanilino)-2,5-dihydrothiophene-4-nitrile (14.09 g, 0.05 mol) dissolved in xylene (150 ml) was added to a solution of chloranil (12.3 g, 0.05 mol) in hot xylene (100 ml). The mixture was allowed to reflux for 2 hours. After cooling, the xylene was evaporated off under vacuum to leave a red-brown solid which was triturated with methanol to give a brick-red solid. The solid was recrystallised from hot methanol to give red crystals which were filtered off, washed with methanol and dried at 50° C. under vacuum. The dried product so obtained was the title compound, m.p. 214° C.

(b) 3-(4-Methylthio-2-nitroanilino)-thiophene-4-nitrile was similarly prepared, m.p. 167°–169° C. (MeOH).

(c) 4-(4-Fluoro-2-nitroanilino)-2-ethyl-thiophene-3-nitrile

EXAMPLE 6

(a) Ethyl 2-(2-aminoanilino)-5-ethyl-thiophene-3-carboxylate

Ethyl-5-ethyl-2-(2-nitroanilino)-thiophene-3-carboxylate (20.7 g) in ethanol (150 ml) was catalytically reduced over 10% palladium on charcoal (2.0 g) at 60 p.s.i. The catalyst was removed by filtration and the solvent removed by distillation in vacuo. The title product so obtained had a melting point of 50°–52° C. (hexane).

The following compounds were similarly prepared:

(b) Ethyl 2-(2-amino-4-fluoroanilino)-5-ethyl-thiophene-3-carboxylate m.p. 82°–84° C. (hexane).

(c) Ethyl 2-(2-amino-3,5-difluoroanilino)-5-ethyl-thiophene-3-carboxylate m.p. 106° C. (EtOH).

(d) Ethyl 2-(2-amino-5-fluoroanilino)-5-ethyl-thiophene-3-carboxylate m.p. 100°–101° C. (EtOH).

(e) Ethyl 2-(2-amino-4-chloroanilino)-5-ethyl-thiophene-3-carboxylate m.p. 119°–121° C. (EtOH).

(f) Ethyl 2-(2,4-diaminoanilino)-5-ethyl-thiophene-3-carboxylate m.p. 152°–5° C. (hexane).

(g) Ethyl 2-(2-amino-4-trifluoromethylanilino)-5-ethyl-thiophene-3-carboxylate (h) Ethyl 2-(2-amino-5-methylanilino)-5-ethyl-thiophene-3-carboxylate (i) Ethyl 2-(4-difluoromethyl-2-nitroanilino)-5-ethyl-thiophene-3-carboxylate (j) Methyl 2-(2-amino-4-N,N-dimethylsulphonamidoanilino)-5-ethyl-thiophene-3-carboxylate (k) Methyl 2-(2-amino-4-methoxyanilino)-5-ethyl-thiophene-3-carboxylate (l) Ethyl 2-(2-amino-4-fluoroanilino)-4,5,6,7-tetrahydrobenzo[b]-thiophene-3-carboxylate (m) Ethyl 2-(2-amino-4-fluoroanilino)-thiophene-3-carboxylate (n) Ethyl 2-(2-amino-4-methylthioanilino)-5-ethyl-thiophene-3-carboxylate (o) Methyl 3-(2-aminoanilino)-thiophene-2-carboxylate m.p. 102° C.

The title compound was prepared by the reduction of methyl 3-(2-nitroanilino)-thiophene-2-carboxylate.

(p) Methyl 3-(2-amino-4-fluoroanilino)-thiophene-2-carboxylate

The title compound was similarly prepared by the reduction of methyl 3-(4-fluoro-2-nitroanilino)-thiophene-2-carboxylate.

(q) Methyl 3-(2-amino-4-chloroanilino)-thiophene-2-carboxylate (r) Methyl 2-(2-amino-4-fluoroanilino)-5-methyl-thiophene-3-carboxylate m.p. 116°–118° C.

(s) Ethyl 5-i-propyl-2-(4-fluoro-2-aminoanilino)-thiophene-3-carboxylate (t) Ethyl 5-n-hexyl-2-(4-fluoro-2-aminoanilino)-thiophene-3-carboxylate (u) Ethyl 4-methyl-2-(4-fluoro-2-aminoanilino)-thiophene-3-carboxylate (v) Ethyl 4-methyl-5-ethyl-2-(4-fluoro-2-aminoanilino)-thiophene-3-carboxylate (w) 2-(2-Aminoanilino)-5-ethyl-thiophene-3-carboxylic acid 5-Ethyl-2-(2-nitroanilino)-thiophene-3-carboxylic acid (8.0 g, 0.027 mol) in ethanol (150 ml) was catalytically reduced over 10% palladium on charcoal (900 mg) at 60 p.s.i. The catalyst was removed by filtration and the solvent removed by distillation in vacuo to give the title compound.

(x) Methyl 5-ethyl-3-(2-amino-4-fluoroanilino)-thiophene-2-carboxylate

EXAMPLE 7

Ethyl 2-(2-amino-4-nitroanilino)-5-ethyl-thiophene-3-carboxylate

Ethyl 2-(2,4-dinitroanilino)-5-ethyl-thiophene-3-carboxylate (0.5 g) in 6N ammonia (25 ml) and ethanol (10 ml) was stirred at reflux temperature and hydrogen sulphide gas passed in over a period of 2 hours. The reaction mixture was cooled to room temperature and the title compound obtained as a yellow precipitate filtered off, washed with water, and dried in vacuo, m.p. 174°–176° C. (EtOAc).

EXAMPLE 8

Ethyl 2-(2-amino-4-bromoanilino)-5-ethyl-thiophene-3-carboxylate

Ethyl 2-(4-bromo-2-nitroanilino)-5-ethyl-thiophene-3-carboxylate (0.4 g, (0.001 mol) was added to powdered zinc (0.4 g) and ammonium chloride (0.4 g) in water (10 ml) and stirred at 50° C. for 24 hours. The reaction mixture was filtered and the recovered solid washed successively with water and ethyl acetate. The organic phase was separated, washed with water, dried ($MgSO_4$) and evaporated in vacuo to give the title compound.

EXAMPLE 9

(a) Methyl 3-(2-Aminoanilino)-2,5-dihyrothiophene-4-carboxylate

3-Carboxymethyltetrahydrothiophen-4-one (48.06 g, 0.3 m) and o-phenylenediamine (32.4 g, 0.3 m) were dissolved in boiling ethanol (500 ml), to which a few drops of acetic acid had been added. The solution was then heated under reflux, in a nitrogen atmosphere for four hours and left to cool. The crystalline material so obtained was filtered off, washed with ethanol and dried under vacuum. The product was recrystallised from absolute ethanol using activated charcoal as a decolouriser, a yellow solution being obtained from which white needles crystallised out. The white crystalline solid was filtered off, washed with ethanol and dried under vacuum to give the title product, m.p. 101° C.

(b) Methyl 3-(2-amino-4,5-dichloroanilino)-2,5-dihydrothiophene-3-carboxylate

The title compound, m.p. 162° C, was obtained by a process similar to that of Example 9(a).

EXAMPLE 10

(a) 3-(2-Aminoanilino)thiophene-4-carboxylate

Methyl 3-(2-aminoanilino)-2,5-dihydrothiophene-4-carboxylate (25.03 g, 0.1 mol) and cloranil (24.6 g, 0.1 mol) were refluxed together in xylene (900 ml) for two hours. The solvent was then evaporated off, under vacuum to leave a dark brown solid which was triturated with ethyl acetate to give a light brown solid, which was filtered, washed with ethyl acetate and dried under vacuum to give the title product, melting point 120°–122° C.

Similarly prepared was:

(b) Methyl 3-(2-amino-4,5-dichloroanilino)-thiophene-4-carboxylate m.p. 162°–163° C.

EXAMPLE 11

Methyl 3-(2-aminoanilino)-thiophene-4-carboxylate

Methyl 3-(2-aminoanilino)-2,5-dihydrothiophene-4-carboxylate (2.5 g, 0.001 mol) was added to a flask contining palladium on charcoal catalyst (5%, 200 mg) in cyclohexene (or norbornadiene or norbornylene) (50 ml) and the reaction was heated at reflux with stirring for 4 hours, the reaction being followed by t.l.c.

The reaction mixture was then cooled, the solvent evaporated off under vacuum to leave a dark brown oil which was column chromatographed using a "Florisil" column and chloroform to give the title product as an orange solid, m.p. 120°–122° C.

EXAMPLE 12

(a) 3-(2-Amino-5-trifluoromethylanilino)-2,5-dihydro-thiophene-4-nitrile

4-Trifluoromethyl-o-phenylenediamine (24 g, 0.136 mol) and 3-keto-4-nitrile-2,5-dihydrothiophene (17.3 g, 0.136 mol) were dissolved in 200 ml of warm ethanol, acetic acid (3 ml) was added and the solution heated under reflux for 24 hours, then left to cool. The title product was thus obtained as a white solid which was filtered off and combined with solid obtained from evaporating the filtrate to small bulk, and cooling, m.p. 189° C.

Similarly prepared were:

(b) 3-(2-Amino-5-chloroanilino)-2,5-dihydrothiophene-4-nitrile m.p. 164°–165° C.

(c) 3-(2-Aminoanilino)-2,5-dihydrothiophene-4-nitrile

3-Keto-4-cyanotetrahydrothiophene (80 g, 0.629 mol) and o-phenylenediamine (68 g, 0.629 mol) were dissolved by heating in 1.5 litres of industrial methylated spirit. To the solution, glacial acetic acid (3 ml) was added, the solution then being heated under reflux with mechanical stirring for 24 hours. The solution was then chilled and filtered to give the title product as a solid, m.p. 163° C.

EXAMPLE 13

(a) 10-Amino-7-chloro-4H-thieno[3,4-b][1,5]benzodiazepine 3-(4-Chloro-2-nitroanilino)-thiophene-4-nitrile (17.18 g, 0.06 mol) was hydrogenated in ethanol (300 ml) and ethyl acetate (100 ml) using a palladium/charcoal catalyst (3.5 g, 10%) in a Parr hydrogenator to give 3-(4-Chloro-2-aminoanilino)-thiophene-4-nitrile. After two hours, the reaction was complete, the catalyst was filtered off and the solution was evaporated to dryness under vacuum.

The light brown solid obtained was redissolved in absolute ethanol (100 ml) in a three-necked flask (500 ml). Concentrated hydrochloric acid (12 ml) was added dropwise carefully to the stirred solution. The alcoholic solution was then allowed to reflux for approximately 24 hours. Sodium hydroxide solution (10%, 60 ml) was then added dropwise to the cooled solution until the solution was slightly basic. During addition, a precipitate of the title compound was formed, which was filtered off to give a pale yellow/brown solid, which was washed with water and dried at 50° C. under vacuum, m.p. 239°-240° C.

Similarly prepared were:

(b)
10-Amino-7-methylthio-4H-thieno[3,4-b][1,5]benzodiazepine, m.p. 195°-7° C.

(c)
12-Amino-9-fluoro-6H-1,2,3,4-tetrahydrobenzothieno[2,3-b][1,5]benzodiazepine (d)
10-Amino-2-ethyl-7-fluoro-4H-thieno[2,3-b][1,5]benzodiazepine (e)
10-Amino-2-ethyl-7-methoxy-4H-thieno[2,3-b][1,5]benzodiazepine (f)
10-Amino-2-ethyl-7-methylthio-4H-thieno[2,3-b][1,5]benzodiazepine (g)
10-Amino-2-ethyl-7-trifluoromethyl-4H-thieno[2,3-b][1,5]benzodiazepine (h)
10-Amino-1-ethyl-7-fluoro-4H-thieno[3,4-b][1,5]benzodiazepine

EXAMPLE 14

(a)
10-Amino-4H-2,5-dihydrothieno[3,4-b][1,5]benzodiazepine hydrochloride 3-(2-Aminoanilino)-2,5-dihydrothiophene-4-nitrile (84.5 g, 0.39 mol) was suspended by mechanical stirring in hot industrial methylated spirit (1.5 liters). Concentrated hydrochloric acid (57 ml, 0.66 mol) was added dropwise, the solution was stirred at reflux temperature for 1 hour then chilled, and the solid so obtained filtered, washed with a little industrial methylated spirit, petrol (40°-60° C.) and dried at 50° C. under vacuum. The title compound so obtained had a melting point of 292° C. (decomp.).

(b)
10-Amino-4H-2,5-dihydrothieno[3,4-b][1,5]benzodiazepine

The hydrochloride of (a) above (54.5 g) was suspended in 1 liter of chloroform with mechanical stirring and 500 ml. of 10% w/w sodium hydroxide was added in one portion. The suspension was stirred for 2 hours whereupon the title compound was obtained as a white solid. This was filtered off, washed with water, ethanol, ether and dried under vacuum to give the free base, m.p. 240°-250° C. (decomp.).

(c)
9,10-Dihydro-4H-2,5-dihydro-thieno[3,4-b][1,5]benzodiazepin-10-one

Methyl 3-(2-aminoanilino)-2,5-dihydrothiophene-4-carboxylate (0.5 g, 0.002 mol) in dry DMSO (2 ml) was added to a solution of 50% w/w sodium hydride/oil suspension (300 mg) in dry DMSO at 90° C. under nitrogen. When effervescence had ceased, the solution was stirred for 2 hours and poured onto 300 ml. of ice/brine. The solution was then extracted into ethyl acetate, the extract dried with magnesium sulphate, filtered and evaporated to small bulk. Ether was added to the suspension and this was filtered. The filtrate was evaporated to dryness and triturated with chloroform to yield the title compound as a yellow solid, m.p. 210° C. (decomposition).

EXAMPLE 15

(a)
10-Amino-4H-2,5-dihydrothieno[3,4-b][1,5]benzodiazepine 3-cyanotetrahydrothiophen-4-one (80 g, 0.629 mol) and o-phenylenediamine (68 g, 0.629 mol) were dissolved in 1.5 liters of industrial methylated spirit by heating under reflux with stirring, acetic acid (3 ml) was then added and the mixture heated under reflux with stirring for 5 hours. To the cooled solution there was carefully added concentrated hydrochloric acid (92 ml, 1.08 mol) with stirring. The solution was then heated under reflux for one hour and to the chilled, stirred solution of hydrochloride there was added 10% w/w sodium hydroxide (500 ml) dropwise, keeping the temperature below 40° C. The solution was then stirred for one hour, the solid filtered off, washed with water, ethanol, acetone, ether, dried under vaccum. The dried product, which was the title compound, had an m.p. of 230°-240° C. (decomp.).

(b) 10-Amino-4H-thieno[3,4-b][1,5]benzodiazepine

10-Amino-4H-2,5-dihydrothieno[3,4-b][1,5]benzodiazepine (43 g, 0.198 mol) was suspended with mechanical stirring in boiling xylene (1 liter). To this was added chloranil (49 g), the suspension being stirred at reflux temperature for 2-6 hours and then left to stand overnight at room temperature. The suspension was then filtered, and the solid washed with xylene until the washings were colourless. It was then dried on a filter funnel. The dried black solid thus obtained was suspended in hot water (200 ml) and 5M hydrochloric acid (36 ml) was added to form a red solution which was boiled for 10 minutes.

The solution was then filtered and residual tar extracted with another 36 ml of 5M HCl in water (200 ml) and refiltered. The collected hot filtrates were added dropwise to an ice-cooled solution of sodium hydroxide (14.4 g, 0.36 mol) in water (100 ml) at such a rate that the temperature of 40° C. was not exceeded. The solution was stirred for 1 hour, filtered, the solid being washed with water and dried under vacuum at 50° C. The dried title compound thus obtained has a melting point of 190° C. (decomp).

EXAMPLE 16

(a)
10-Amino-6-trifluoromethyl-4H-2,5-dihydrothieno[3,4-b][1,5]benzodiazepine 3-(2-Amino-5-trifluoromethylanilino)-4-cyano-2,5-dihydrothiophene (10.5 g, 0.0368 mol) was dissolved in industrial methylated spirit (100 ml) by heating, and to this stirred solution, a solution of concentrated hydrochloric acid (3.2 ml, 0.0368 mol) was carefully added. The red solution so formed was heated under reflux for 1 hour. To the chilled, stirred solution, a solution of sodium hydroxide (1.6 g) in water (10 ml) was added dropwise, the temperature being kept below 40° C. The buff amidine thus formed was filtered off, washed with water, ethanol, 40°-60° C. petrol, and then dried at 50° C. under vacuum. The filtrate was diluted with an excess of water and the solid so produced was filtered off and dried and included with the other solid. The title compound thus produced had a melting point of 200°-210° C. (decomp.).

Similarly prepared was:

(b)

10-Amino-6-chloro-4H-2,5-dihydrothieno[3,4-b][1,5]benzodiazepine

EXAMPLE 17

The product of Examples 16(a) and 16(b) are "aromatised" to (a)

10-Amino-6-trifluoromethyl-4H-thieno[3,4-b][1,5]benzodiazepine, m.p. 178° C. (dec); and (b)

10-Amino-6-chloro-4H-thieno[3,4-b][1,5]benzodiazepine, using the process of Example 15(b).

EXAMPLE 18

(a)

9,10-Dihydro-2-ethyl-4H-thieno[2,3-b][1,5]benzodiazepin-10-one

Sodium methyl sulphinyl carbanion was generated by stirring sodium hydride (7.2 g, 0.15 mol) in dry dimethysulphoxide (100 ml) at 70° C. until gas evolution ceased. Ethyl 2-(2-aminoanilino)-5-ethyl-thiophene-3-carboxylate (14.5 g, 0.05 mol) in dry dimethylsulphoxide (50 ml) was added and stirred for 15 minutes. The mixture was poured onto ice-water (600 ml) and stirred for fifteen minutes. The solid was filtered off, washed well with water, dried, washed with carbon tetrachloride and dried in vacuo at 60° C. The dried product which was the title compound had a melting point of 218°-220° C. (CHCl$_3$).

(b)

2-Ethyl-7-fluoro-9,10-dihydro-4H-thieno[2,3-b][1,5]benzodiazepin-10-one

The title compound, m.p. 210°-212° C., was similarly prepared from ethyl 2-(2-amino-4-fluoroanilino)-5-ethyl-thiophene-3-carboxylate. The title compound was recrystallised from ethanol.

The following compounds were also similarly prepared using the process of Example 18(a). In each case, the starting thiophene material, melting point of title product, and recrystallisation solvent are indicated.

(c)

6,8-Difluoro-9,10-dihydro-2-ethyl-4H-thieno[2,3-b][1,5]benzodiazepin-10-one

Ethyl 2-(2-amino-3,5-difluoroanilino)-5-ethyl-thiophene-3-carboxylate, m.p. 230°-232° C. (CHCl$_3$).

(d)

9,10-Dihydro-2-ethyl-6-fluoro-4H-thieno[2,3-b][1,5]benzodiazepin-10-one

Ethyl 2-(2-amino-5-fluoroanilino)-5-ethyl-thiophene-3-carboxylate, m.p. 255°-257° C. (EtOAc).

(e)

7-Chloro-9,10-dihydro-2-ethyl-4H-thieno[2,3-b][1,5]benzodiazepin-10-one

Ethyl 2-(2-amino-4-chloroanilino)-5-ethyl-thiophene-3-carboxylate, m.p. 216°-218° C. (EtOAc).

(f)

7-Amino-9,10-dihydro-2-ethyl-4H-thieno[2,3-b][1,5]benzodiazepin-10-one

Ethyl 2-(2,4-diaminoanilino)-5-ethyl-thiophene-3-carboxylate, m.p. 230° C. (decomp.) (CHCl$_3$/MeOH).

(g)

9,10-Dihydro-2-ethyl-6-methyl-4H-thieno[2,3-b][1,5]benzodiazepin-10-one 2-(2-Amino-5-methylanilino)-5-ethyl-thiophene-3-carboxylate m.p. 205°-207° C. (EtOAc).

(h)

9,10-Dihydro-7-N,N-dimethylsulphonamido-2-ethyl-4H-thieno[2,3-b][1,5]-benzodiazepin-10-one Methyl 2-(2-amino-4-N,N-dimethylsulphonamidoanilino)-5-ethyl-thiophene-3-carboxylate, m.p. 258°-260° C. (EtOAc).

(i)

9,10-Dihydro-2-ethyl-7-nitro-4H-thieno[2,3-b][1,5]benzodiazepin-10-one

Ethyl 2-(2-amino-4-nitroanilino)-5-ethyl-thiophene-3-carboxylate, m.p. 264°-266° C. (EtOAc).

(j)

9,10-Dihydro-7-fluoro-4H-thieno[2,3-b][1,5]benzodiazepin-10-one

Ethyl 2-(2-amino-4-fluoroanilino)-thiophene-3-carboxylate, m.p. 235°-240° C. (CCl$_4$/hexane).

(k)

9-Fluoro-6H-1,2,3,4,11,12-hexahydrobenzothieno[2,3-b][1,5]benzodiazepin-12-one

Ethyl 2-(2-amino-4-fluoroanilino)4,5,6,7-tetrahydrobenzo[b]thiophene-3-carboxylate m.p. 238° C. (EtOAc).

(l)

9,10-Dihydro-2-ethyl-7-trifluoromethyl-4H-thieno[2,3-b][1,5]benzodiazepin-10-one Ethyl 2-(2-amino-4-trifluoromethylanilino)-5-ethyl-thiophene-3-carboxylate.

(m)

9,10-Dihydro-2-ethyl-7-methoxy-4H-thieno[2,3-b][1,5]benzodiazepin-10-one

Ethyl 2-(2-amino-4-methoxyanilino)-5-ethyl-thiophene-3-carboxylate.

(n)

9,10-Dihydro-2-ethyl-7-methylthio-4H-thieno[2,3-b][1,5]benzodiazepin-10-one

Ethyl 2-(2-amino-4-methylthioanilino)-5-ethyl-thiophene-3-carboxylate.

(o)

6,7-Difluoro-9,10-dihydro-2-ethyl-4H-thieno[2,3-b][1,5]benzodiazepin-10-one

Ethyl 5-ethyl-2-(4,5-difluoro-2-nitroanilino)-thiophene-3-carboxylate, m.p. 290° C.

(p)
9,10-Dihydro-7-fluoro-2-phenyl-4H-thieno[2,3-b][1,5]benzodiazepin-10-one m.p. 250°-252° C. (dec.) (EtOAc).

(q)
9,10-Dihydro-7-fluoro-2-methyl-4H-thieno[2,3-b][1,5]benzodiazepin-10-one m.p. 250°-252° C. (EtOAc).

(r)
9,10-Dihydro-4H-thieno[3,2-b][1,5]benzodiazepin-10-one

Methyl 3-(2-aminoanilino)-thiophene-2-carboxylate, m.p. 226° C. (CCl₄).

(s)
9,10-Dihydro-7-fluoro-4H-thieno[3,2-b][1,5]benzodiazepin-10-one

Methyl 3-(2-amino-4-fluoroanilino)-thiophene-2-carboxylate, m.p. 225°-230° C. (EtOAc).

(t)
7-Chloro-9,10-dihydro-4H-thieno[3,2-b][1,5]benzodiazepin-10-one

Methyl 3-(2-amino-4-chloroanilino)-thiophene-2-carboxylate, m.p. 255°-256° C. (EtOAc).

(u)
9,10-Dihydro-4H-thieno[3,4-b][1,5]benzodiazepin-10-one m.p. 233°-234° C.

(v)
9,10-Dihydro-7-fluoro-4H-thieno[3,4-b][1,5]benzodiazepin-10-one

Melting pont 238° C. (decomposition).

(w)
6,7-Dichloro-9,10-dihydro-4H-thieno[3,4-b][1,5]benzodiazepin-10-one

Melting point 284°-287° C.

(x)
2-i-Propyl-7-fluoro-9,10-dihydro-4H-thieno[2,3-b][1,5]benzodiazepin-10-one (y)
2-n-Hexyl-7-fluoro-9,10-dihydro-4H-thieno[2,3-b][1,5]benzodiazepin-10-one (z)
1-Methyl-7-fluoro-9,10-dihydro-4H-thieno[2,3-b][1,5]benzodiazepin-10-one (aa)
1-Methyl-2-ethyl-7-fluoro-9,10-dihydro-4H-thieno[2,3-b][1,5]benzodiazepin-10-one (bb)
2-Ethyl-7-fluoro-9,10-dihydro-4H-thieno[3,2-b][1,5]benzodiazepin-10-one (cc)
2-Ethyl-9,10-dihydro-4H-thieno-[2,3-b][1,5]benzodiazepin-10-one 5-Ethyl-2-(2-aminoanilino)-thiophene-3-carboxylic acid was dissolved in tetrahydrofuran (distilled from lithium aluminium hydride) (200 ml) and solid dicyclohexylcarbodiimide (5.7 g, 0.027 mol) added. The mixture was stirred under a nitrogen atmosphere for 16 hours and the solution thus formed filtered and evaporated to dryness. The residue was boiled with carbon tetrachloride and allowed to crystallise to yield the title compound, m.p. 218°-220° C. (CHCl₃).

EXAMPLE 19

(a)
7-Chloro-9,10-dihydro-4H-thieno[3,4-b][1,5]benzodiazepin-10-one

10-Amino-7-chloro-4H-thieno[3,4-b][1,5]benzodiazepine (4 g, 0.15 mol) was dissolved in the minimum of water (100 ml) to which was added potassium carbonate (13.0 g) in water (20 ml). Absolute ethanol (40 ml) was then added to redissolve the amidine and the reaction mixture gently refluxed for 17 hours, during the last hour of which, the ethanol was slowly distilled off.

The reaction mixture was then allowed to cool, and concentrated hydrochloric acid added dropwise to the solution, in the presence of ethyl acetate, until the solution was slightly acidic. The aqueous phase was extracted with ethyl acetate, dried over MgSO₄ and the bulked extracts evaporated to dryness under vaccuum, the title product being obtained as a light brown solid. The solid was triturated with ether, filtered and dried at 50° C. under vacuum to give a yellow solid, m.p. 212°-213° C.

Using the hydrolytic procedure of Example 19(a) the following other amides were obtained:

(b)
9,10-Dihydro-4H-thieno[3,4-b][1,5]benzodiazepin-10-one

Melting point 234° C. (decomp.).

(c)
9,10-Dihydro-7-methylthio-4H-thieno[3,4-b][1,5]benzodiazepin-10-one (d)
9,10-Dihydro-6-trifluoromethyl-4H-thieno[3,4-b][1,5]benzodiazepin-10-one, m.p. 213° C.

(e)
9,10-Dihydro-2-ethyl-7-fluoro-4H-thieno[2,3-b][1,5]benzodiazepin-10-one m.p. 211° C.

(f)
9,10-Dihydro-2-ethyl-7-fluoro-4H-thieno[2,3-b][1,5]benzodiazepin-10-one (g)
9,10-Dihydro-2-ethyl-7-methylthio-4H-thieno[2,3-b][1,5]benzodiazepin-10-one (h)
9,10-Dihydro-2-ethyl-7-trifluoromethyl-4H-thieno[2,3-b][1,5]benzodiazepin-10-one (i)
9-Fluoro-6H-1,2,3,4,11,12-hexahydrobenzothieno[2,3-b][1,5]benzodiazepin-12-one (j)
9,10-Dihydro-2-ethyl-6-trifluoromethyl-4H-thieno[2,3-b][1,5]benzodiazepin-10-one (k)
1-Ethyl-7-fluoro-4H-thieno[3,4-b][1,5]benzodiazepin-10-one

EXAMPLE 20

9,10-Dihydro-4H-thieno[3,4-b][1,5]benzodiazepin-10-one 9,10-Dihydro-4H-2,5-dihydrothieno[3,4-b][1,5]benzodiazepin-10-one (0.33 g) was stirred in cyclohexene (norbornadiene or norbornylene) at reflux temperatures in the presence of a palladium on charcoal catalyst (0.1 g, 5%), the reaction being followed by t.l.c. measurements.

The reaction mixture was then cooled, the solvent evaporated off under vacuum to leave dark brown solid which was column chromatographed using a "Florisil" column and 5% methanol in chloroform to give the title compound as a pale yellow solid, m.p. 230°–232° C.

EXAMPLE 21

7-N-Acylamino-9,10-dihydro-2-ethyl-4H-thieno[2,3-b][1,5]benzodiazepin-10-one

7-Amino-9,10-dihydro-2-ethyl-4H-thieno[2,3-b][1,5]benzodiazepin-10-one (100 mg) was suspended in methylene chloride (5 ml) and triethylamine (0.1 ml). Acetic anhydride (10.1 ml) was added and the reaction mixture stirred for 18 hours. The precipitate was filtered off, washed with water, dried in vacuo at 60° C. to give the title compound as a solid, m.p. 264° C.

EXAMPLE 22

3-Chloro-9,10-dihydro-4H-thieno[3,4-b][1,5]benzodiazepin-10-one

4H-Thieno[3,4-b][1,5]benzodiazepin-10-one (4.32 g, 0.02 mol) in hot dichloromethane was reacted with stirring, with N-chlorosuccinimide (3.0 g, 0.025 mol) in the presence of a trace of benzoyl peroxide. After refluxing for 1 hour the hot solution was filtered. The blue residue was washed with three quantities of hot ethyl alcohol which were combined and bulked with the dichloromethane filtrate and evaporated to a brown solid. Soxhlet extraction with benzene and subsequent washing with $K_2CO_3$ solution, drying and evaporation yielded the title compound as a buff solid m.p. 229° C.

EXAMPLE 23

1-Acetyl-9,10-dihydro-2-ethyl-7-fluoro-4H-thieno[2,3-b][1,5]benzodiazepin-10-one To a stirred solution of 9,10-dihydro-2-ethyl-7-fluoro-4H-thieno[2,3-b][1,5]benzodiazepine (0.26 g, 0.001 mol) in acetyl chloride (3 ml) was added with stirring stannic chloride (2 drops). The reaction was diluted with benzene (5 ml) and stirred for 18 hours at room temperature. The reaction mixture was diluted with water and extracted into chloroform, the chloroform extracts were washed with water, dried (MgSO$_4$) and evaporated in vacuo to give the title product as a solid, m.p. 215°–218° C. (MeOH/hexane).

EXAMPLE 24

(a)
9,10-Dihydro-2-ethyl-7-fluoro-4H-thieno[2,3-b][1,5]benzodiazepin-10-thione 9,10-Dihydro-2-ethyl-7-fluoro-4H-thieno[2,3-b][1,5]benzodiazepin-10-one (20 g, 0.076 mol) was added to a stirred solution of phosphorus pentasulphide (17 g, 0.076 mol) in dry pyridine (400 ml). The solution was stirred at gentle reflux for 1.5 hours, poured onto ice-water, stirred for 1 hour, filtered, washed with cold water and dried. Recrystallisation from EtOH/water gave the title compound as bronze plates m.p. 203°–206° C.

(b)
9,10-Dihydro-2-ethyl-4H-thieno[2,3-b][1,5]benzodiazepin-10-thione

The title compound was similarly prepared using the process of Example 24(a) with 9,10-dihydro-2-ethyl-4H-thieno[2,3-b][1,5]benzodiazepin-10-one as starting material, m.p. 233°–236° C. (EtOH—H$_2$O).

Similarly prepared were:

(c)
9,10-Dihydro-2-ethyl-7-nitro-4H-thieno[2,3-b][1,5]benzodiazepin-10-thione (d)
9,10-Dihydro-4H-thieno[3,4-b][1,5]benzodiazepin-10-thione, m.p. 221° C.

Other amides of Example 18 were similarly converted into their thioamidederivatives using the procedure of Example 24(a). In each case, the identification and confirmation of the final product was effected by means of t.l.c. and microanalytical evidence.

EXAMPLE 25

(a)
2-Ethyl-6-fluoro-10-(4-methyl-1-piperazinyl)-4H-thieno[2,3-b][1,5]benzodiazepine 9,10-Dihydro-2-ethyl-6-fluoro-4H-thieno[2,3-b][1,5]benzodiazepin-10-one (0.5 g), phosphorous oxychloride (4 ml) and N,N-dimethylaniline (0.15 ml) were refluxed for 3 hours. The reaction mixture was evaporated in vacuo and the residue evaporated twice more with xylene. The crude imino chloride was dissolved in absolute dioxan (1 ml) and N-methyl piperazine (3 ml) added. The reaction was refluxed for 4 hours and then evaporated to dryness in vacuo. The residue was partitioned between aqueous ammonia and ether and the ether phase extracted with N,HCl. The product was precipitated by the addition of 0.88 ammonia and extracted into ether, washed with water, dried (MgSO₄) and evaporated in vacuo, m.p. 175°–177° C. (EtOAc/hexane).

Similarly prepared was:

(b)

2-Ethyl-7-fluoro-10-(1-piperazinyl)-4H-thieno[2,3-b][1,5]benzodiazepine, m.p. 138°–140° C. (CCl₄/hexane)

EXAMPLE 26

(a)

2-Ethyl-10-(4-methyl-1-piperazinyl)-4H-thieno[2,3-b][1,5]benzodiazepine 9,10-Dihydro-2-ethyl-4H-thieno[2,3-b][1,5]benzodiazepin-10-one (2.4 g, 0.01 mol) was suspended in N-methyl piperazine (10 ml). Titanium tetrachloride (1.2 ml, 0.011 mol) in dry anisole (5 ml) was added and the mixture stirred and heated at 120° C. for 2 hours. The reaction was poured onto ice-water and shaken until a greyish white precipitate formed. The suspension was extracted with methylene chloride until no more yellow colour was removed. The combined extracts were washed with water, dried (MgSO₄) and evaporated in vacuo to yield the title compound as a yellow solid. This solid was triturated with ether, filtered, and recrystallised from hexane, m.p. 195°–197° C.

The free base was then converted to its maleate salt, m.p. 186°–188° C. (ethanol/ether).

(b)

2-Ethyl-7-fluoro-10-(4-methyl-1-piperazinyl)-4H-thieno[2,3-b][1,5]benzodiazepine The title compound, m.p. 161°–163° C. (hexane), was prepared using a procedure similar to that of Example 26(a) from 9,10-dihydro-2-ethyl-7-fluoro-4H-thieno[2,3-b][1,5]benzodiazepin-10-one.

Anal.Calc. for $C_{18}H_{21}FN_4S$: C; 62.76; H: 6.14; N: 16.26; f; 5.51; S: 9.30%. Found: C: 62.99; H: 5.87; N: 16.06; F: 5.67; S: 9.32%.

The free base was converted to its maleate salt, m.p. 125°–127° C. (ethanol-ether).

Anal.Calc. for $C_{22}H_{25}FN_4O_4S$: C: 57.37; H: 5.47; N: 12.16; F: 4.12; S: 6.96%. Found: C: 57.53; H: 5.54; N: 11.99; F: 4.16; S: 6.93%.

The following benzodiazepines were similarly prepared using the process of Example 26(a). The material given beneath the title is the amide intermediate, the melting point is that of the title product and the recrystallisation solvent is indicated in parentheses.

(c)

2-Ethyl-6-fluoro-10-(4-methyl-1-piperazinyl)-4H-thieno[2,3-b][1,5]benzodiazepine 9,10-Dihydro-2-ethyl-6-fluoro-4H-thieno[2,3-b][1,5]benzodiazepin-10-one, m.p. 206°–208° C. (hexane); maleate salt, m.p. 125°–127° C. (EtOH/Et₂O).

(d)

6,8-Difluoro-2-ethyl-10-(4-methyl-1-piperazinyl)-4H-thieno[2,3-b][1,5]benzodiazepine 6,8-Difluoro-9,10-dihydro-2-ethyl-4H-thieno[2,3-b][1,5]benzodiazepin-10-one, m.p. 243°–246° C. (CCl₄/hexane); maleate salt, m.p. 122°–4° C. (EtOH/Et₂O).

(e) 7-Chloro-2-ethyl-10-(4-methyl-b 1-piperazinyl)-4H-thieno[2,3-b][1,5]benzodiazepine 7-Chloro-9,10-dihydro-b 2-ethyl-4H-thieno[2,3-b][1,5]benzodiazepin-10-one, m.p. 235°–240° C.; maleate salt, m.p. 119°–121° C. (EtOH/Et₂O).

(f)

2-Ethyl-6-methyl-10-(4-methyl-1-piperazinyl)-4H-thieno[2,3-b][1,5]benzodiazepine The title compound was similarly prepared using 9,10-dihydro-2-ethyl-6-methyl-4H-thieno[2,3-b][1,5]benzodiazepin-10-one, m.p. 177°–179° C. (CH₂Cl₂/hexane).

(g)

7-N,N-Dimethylsulphonamido-2-ethyl-10-(4-methyl-1-piperazinyl)-4H-thieno[2,3-b][1,5]benzodiazepine 9,10-Dihydro-7-N,N-dimethylsulphonamido-2-ethyl-4H-thieno[2,3-b][1,5]benzodiazepin-10-one, m.p. 225°–227° C. (EtOAc/hexane).

(h)

7-Fluoro-10-(4-methyl-1-piperazinyl)-4H-thieno[2,3-b][1,5]benzodiazepine 9,10-Dihydro-7-fluoro-4H-thieno[2,3-b][1,5]benzodiazepin-10-one, m.p. 228°–230° C. (CH₂Cl₂/hexane).

(i)

9-Fluoro-12-(4-methyl-1-piperazinyl)-6H-1,2,3,4-tetrahydrobenzothieno[2,3-b][1,5]benzodiazepine 9-Fluoro-6H-1,2,3,4,11,12-hexahydrobenzothieno[2,3-b][1,5]benzodiazepin-12-one, m.p. 196°–199° C. (CH₂Cl₂/hexane).

(j)

7-Fluoro-2-methyl-10-(4-methyl-1-piperazinyl)-4H-thieno[2,3-b][1,5]benzodiazepine 7-Fluoro-b 2-methyl-9,10-dihydro-4H-thieno[2,3-b][1,5]benzodiazepin-10-one, m.p. 160°–165° C. (dec.) (EtOAc/hexane).

(k)

7-Fluoro-2-phenyl-10-(4-methyl-1-piperazinyl)-4H-thieno[2,3-b][1,5]benzodiazepine, dihydrochloride The free base of the chloride identified above was prepared using 7-fluoro-2-methyl-9,10-dihydro-4H-thieno[2,3-b][1,5]benzodiazepin-10-one. This was then converted to the dihydrochloride, m.p. 235°–240° C. (dec.) (MeOH/hexane).

(l)

7-Trifluoromethyl-2-ethyl-10-(4-methyl-1-piperazinyl)-4H-thieno[2,3-b][1,5]benzodiazepine 7-Trifluoromethyl-2-ethyl-9,10-dihydro-4H-thieno[2,3-b][1,5]benzodiazepin-10-one.

(m)

10-(4-Methyl-1-piperazinyl)-4H-thieno[3,2-b][1,5]benzodiazepine 9,10-Dihydro-4H-thieno[3,2-b][1,5]benzodiazepin-10-one, m.p. 202°–206° C. (CCl₄).

(n)

7-Fluoro-10-(4-methyl-1-piperazinyl)-4H-thieno[3,2-b][1,5]benzodiazepine

7-Fluoro-9,10-dihydro-4H-thieno[3,2-b][1,5]benzodiazepin-10-one, m.p. 206°–208° C.

(o)

7-Chloro-10-(4-methyl-1-piperazinyl)-4H-thieno[3,2-b][1,5]benzodiazepine

7-Chloro-9,10-dihydro-4H-thieno[3,2-b][1,5]benzodiazepin-10-one, m.p. 225°–226° C. ($CHCl_3$).

(p)

7-Chloro-10-(4-methyl-1-piperazinyl)-4H-thieno[3,4-b][1,5]benzodiazepine

7-Chloro-9,10-dihydro-4H-thieno[3,4-b][1,5]benzodiazepin-10-one, m.p. 169°–170° C.

(q)

7-Methylthio-10-(4-methyl-1-piperazinyl)-4H-thieno[3,4-b][1,5]benzodiazepine (r)

10-(4-Methyl-1-piperazinyl)-7-trifluoromethyl-4H-thieno[3,4-b][1,5]benzodiazepine 6-Trifluoromethyl-9,10-dihydro-4H-thieno[3,4-b][1,5]benzodiazepin-10-one, m.p. 202° C. ($CCl_4$/petrol 40°–60° C.).

(s)

3-Chloro-10-(4-methyl-1-piperazinyl)-4H-thieno[3,4-b][1,5]benzodiazepine

3-Chloro-9,10-dihydro-4H-thieno[3,4-b][1,5]benzodiazepin-10-one.

(t)

10-(4-Methyl-1-piperazinyl)-4H-thieno[3,4-b][1,5]benzodiazepine m.p. 200°–201° C.

(u)

7-Fluoro-10-(4-methyl-1-piperazinyl)-4H-thieno[3,4-b][1,5]benzodiazepine m.p. 190.5°–191.5° C.

(v)

6,7-Dichloro-10-(4-methyl-1-piperazinyl)-4H-thieno[3,4-b][1,5]benzodiazepine m.p. 200°–202° C.

(w)

2-i-Propyl-7-fluoro-10-(4-methyl-1-piperazinyl)-4H-thieno[2,3-b][1,5]benzodiazepine (x)

2-n-Hexyl-7-fluoro-10-(4-methyl-1-piperazinyl)-4H-thieno[2,3-b][1,5]benzodiazepine (y)

1-Methyl-7-fluoro-10-(4-methyl-1-piperazinyl)-4H-thieno[2,3-b][1,5]benzodiazepine (z)

1-Methyl-2-ethyl-7-fluoro-10-(4-methyl-1-piperazinyl)-4H-thieno[2,3-b][1,5]benzodiazepine (aa)

6,7-Difluoro-2-ethyl-10-(4-methyl-1-piperazinyl)-4H-thieno[2,3-b][1,5]benzodiazepine, m.p. 172° C. ($CCl_4$/hexane).

(bb)

7-Fluoro-10-(4-methyl-1-piperazinyl)-1-ethyl-4H-thieno[3,4-b][1,5]benzodiazepine (cc)

2-Ethyl-7-fluoro-10-(4-methyl-1-piperazinyl)-4H-thieno[3,2-b][1,5]benzodiazepine

EXAMPLE 27

The processes of Example 26 could be repeated by using the thioamides produced by the process of Example 24 in place of the amides, with production of the benzodiazepines specified in Examples 26(a) to (cc).

EXAMPLE 28

10-(4-Methyl-1-piperazinyl)-4H-thieno[3,4-b][1,5]benzodiazepine 4H-2,5-Dihydrothieno[3,4-b][1,5]benzodiazepin-10-one (10 g) in dry anisole (5 ml) was heated with stirring in the presence of titanium tetrachloride (0.04 ml) and N-methylpiperazine to 120° C. The reaction was quenched after 1½ hours, shaken with ethyl acetate, which was run off, evaporated to dryness at 70° C. under reduced pressure. The solid was column chromatographed down a "Florisil", 5% methanol in chloroform, column. The collected fractions, when evaporated to dryness, yielded the title compound as a yellow solid, m.p. 200°–201° C.

EXAMPLE 29

10-(4-Methyl-1-piperazinyl)-4H-thieno[3,4-b][1,5]benzodiazepine

10-Amino-4H-2,5-dihydro-thieno[3,4-b][1,5]benzodiazepine (2.17 g) in anisole, and N-methylpiperazine (10 ml) were stirred at room temperature in a 100 ml. round-bottomed flask. The complex derived from titanium tetrachloride (2.6 ml) in anisole (15 ml) was added slowly to the stirred mixture. After complete addition, the reaction mixture was stirred under nitrogen and heated to 120° C. The reaction was followed by t.l.c. which witnessed formation of the aromatised starting material before condensation with the N-methylpiperazine. The mixture was heated overnight at 120° C., cooled, and poured into water. The aqueous mixture was made basic with dilute sodium hydroxide solution, and shaken with chloroform. The organic extract was washed with water, dried and evaporated to an oil under vacuum. Column chromatography of the oil on a silicic acid column with 5% methanol in chloroform gave fractions containing the title compound

EXAMPLE 30

10-(4-Methyl-1-piperazinyl)-4H-thieno[3,4-b][1,5]benzodiazepine

10-Amino-4H-thieno[3,4-b][1,5]benzodiazepine (215 mg) in anisole (1 ml) was treated with N-methylpiperazine (2.5 ml) at room temperature under nitrogen. Titanium tetrachloride (0.12 ml) in anisole (1 ml) was added to the stirred mixture at room temperature. The mixture, under nitrogen, was heated to 110° C. and stirred overnight.

The resulting mixture was cooled, poured into water, made basic with dilute sodium hydroxide solution, and shaken with chloroform. The organic solvent was extracted, washed with water, dried and evaporated to an oil under vacuum. The required product was isolated via column chromatography using a silicic acid column with 5% methanol in chloroform to give the title product as a pale yellow solid, m.p. 200°–201° C.

Similarly, the benzodiazepines specified in Examples 26(a) to (cc) were prepared from the corresponding 10-amino derivatives, although in many cases yields were extremely poor.

EXAMPLE 31

(a)

10-(4-Carboethoxy-1-piperazinyl)-2-ethyl-7-fluoro-4H-thieno[2,3-b][1,5]benzodiazepine A suspension of 9,10-dihydro-2-ethyl-7-fluoro-4H-thieno[2,3-b][1,5]benzodiazepin-10-one (2.6 g, 0.01 mol) in a mixture of anisole (5 ml), toluene (10 ml) and ethyl-N-piperazino-carboxylate (9.6 g, 0.06 mol) was treated with a solution of titanium tetrachloride (1.2 ml, 0.011 mol) in dry anisole (5 ml) and toluene (10 ml). The mixture was refluxed for 3 hours and poured into ice-water (200 ml). The aqueous material was extracted with methylene chloride, washed with water, dried (MgSO₄) and evaporated to a gum (5 g). Trituration with ether gave the title product as a yellow solid, m.p. 168°–171° C. (CH₂Cl₂/hexane); maleate salt, m.p. 149°–151° C. (EtOH/Et₂O).

Similarly prepared were:

(b)

10-(4-Carboethoxy-1-piperazinyl)-2-ethyl-4H-thieno[2,3-b][1,5]benzodiazepine m.p. 169° C. (CH₂Cl₂/CCl₄/n-hexane). (c) 10-(4-Carboethoxy-1-piperazinyl)-7-chloro-2ethyl-4H-thieno[2,3-b][1,5]benzodiazepine
m.p. 155°–158° C. (EtOAc/hexane).

The title compound was similarly prepared using 7-chloro-9,10-dihydro-2-ethyl-4H-thieno[2,3-b][1,5]benzodiazepin-10-one, m.p. 155-158° C. (EtOAc/hexane).

(d)

10-(4-Carboethoxy-1-piperazinyl)-2-ethyl-6-fluoro-4H-thieno[2,3-b][1,5]-benzodiazepine m.p. 176°–178° C. (EtOAc/hexane).

(e)

10-(4-Carboethoxy-1-piperazinyl)-4H-thieno[3,2-b][1,5]benzodiazepine m.p. 166° C. (CHCl₃).

(f)

10-(4-Carboethoxy-1-piperazinyl)-7-fluoro-4H-thieno[3,2-b][1,5]benzodiazepine m.p. 162°–164° C. (EtOAc).

(g)

10-(4-Carboethoxy-1-piperazinyl)-4H-thieno[3,4-b][1,5]benzodiazepine m.p. 186°–187° C.

(h)

10-(4-Carboethoxy-1-piperazinyl)-7-fluoro-4H-thieno[3,4-b][1,5]benzodiazepine m.p. 197°–199° C.

(i)

10-(4-Carboxyethyl-1-piperazinyl)-6,7-dichloro-4H-thieno[3,4-b][1,5]benzodiazepine m.p. 213°–214° C.

(j)

10-(4-Carboxyethyl-1-piperazinyl)-7-chloro-4H-thieno[3,4-b][1,5]benzodiazepine.

m.p. 195°–196° C.

EXAMPLE 32

(a)

2-Ethyl-7-fluoro-10-(1-piperazinyl)-4H-thieno[2,3-b][1,5]benzodiazepine 10-(4-carboethoxy-1-piperazinyl)-2-ethyl-7-fluoro-4H-thieno[2,3-b][1,5]benzodiazepine (1.0 g), and potassium hydroxide pellets (6.0 g) in 96% ethanol (50 ml) were refluxed for 16 hours. The resulting suspension was evaporated to dryness and partitioned between water and chloroform. The chloroform layer was washed with water, dried (MgSO₄) and evaporated to give the title product as a yellow solid, m.p. 138°–140° C (CCl₄/hexane).

The following benzodiazepines were similarly prepared:

(b)

2-Ethyl-10-(1-piperzinyl)-4H-thieno[2,3-b][1,5]benzodiazepine m.p. 170°–171° C. (EtOAc/hexane).

7-Chloro-2-ethyl-10-(1-piperazinyl)-4H-thieno[2,3-b][1,5]benzodiazepine m.p. 167°–169° C.

(d)

10-(1-Piperazinyl)-4H-thieno[3,2-b][1,5]benzodiazepine m.p. 203°–206° C. (EtOAc).

(e)

7-Fluoro-10-(1-piperazinyl)-4H-thieno[3,2-b][1,5]benzodiazepine m.p. 165°–167° C. (CCl₄)

(f)

10-(1-Piperazinyl)-4H-thieno[3,4-b][1,5]benzodiazepine m.p. 233°–235° C.

(g)
7-Fluoro-10-(1-piperazinyl)-4H-thieno[3,4-b][1,5]benzodiazepine m.p. 192°-193° C.

(h)
6,7-Dichloro-10-(1-piperazinyl)-4H-thieno[3,4-b][1,5]benzodiazepine m.p. 213°-214° C.
(i) 7-Chloro-10-(1-piperazinyl)-4H-thieno[3,4-b][1,5]benzodiazepine
m.p. 178°-179° C.

EXAMPLE 33

(a)
10-(4-p-Chlorobenzyl-1-piperazinyl)-2-ethyl-7-fluoro-4H-thieno[2,3-b][1,5]benzodiazepine 2-Ethyl-7-fluoro-10-(1-piperazinyl)-4H-thieno[2,3-b][1,5]benzodiazepine (1.0 g, 0.003 mol), p-chlorobenzyl chloride (0.38 ml, 0.0033 mol) and triethylamine (1.0 ml) in 90% ethanol (25 ml) was refluxed for 16 hours. The reaction mixture was evaporated to dryness and partitioned between water and methylene chloride. The organic extracts were washed with water, dried (MgSO$_4$) and evaporated in vacuo to yield the title product as a solid, melting point 166°-168° C. when recrystallised from CH$_2$Cl$_2$/hexane.

The following compounds were similarly prepared:

(b)
10-(4-Benzyl-1-piperazinyl)-2-ethyl-4H-thieno[2,3-b][1,5]benzodiazepine m.p. 79°-80° C.

However, in this reaction benzyl bromide was as the alkylating agent.

(c)
10-(4'-Benzyl-1'-piperazinyl)-4H-thieno[3,2-b][1,5]benzodiazepine m.p. 198°-200° C. (EtOAc).

(d)
7-Fluoro-10-(4'-benzyl-1'-piperazinyl)-4H-thieno[3,2-b][1,5]benzodiazepine m.p. 180°-182° C. (CHCl$_3$).

(e)
10-(4-Benzyl-1-piperazinyl)-4H-thieno[3,4-b][1,5]benzodiazepine m.p. 221°-222.5° C.

(f)
2-Ethyl-7-fluoro-10-(4-cyclopropyl-1-piperazinyl)-4H-thieno[2,3-b][1,5]benzodiazepine

EXAMPLE 34

(a)
2-Ethyl-7-fluoro-10-[4-(2-hydroxyethyl)-1-piperazinyl]-4H-thieno[2,3-b][1,5]benzodiazepine 2-Ethyl-7-fluoro-10-(1-piperazinyl)-4H-thieno[2,3-b][1,5]benzodiazepine (1.65 g, 0.005 mol) and ethylene bromohydrin (1.25 g, 0.01 mol) in 90% ethanol (150 ml) and triethylamine (2.02 g, 0.02 mol) were refluxed under a nitrogen atmosphere for 16 hours. The reaction mixture was evaporated to dryness, partitioned between water and methylene chloride, the methylene chloride extract washed with water, dried (MgSO$_4$) and evaporated to dryness to yield the title compound as a solid, m.p. 173°-175° C. (CH$_2$Cl$_2$/hexane).

Similarly prepared were:

(b)
7-Fluoro-10-[4-(2-hydroxyethyl)-1-piperazinyl]-4H-thieno[3,2-b][1,5]benzodiazepine m.p. 205°-210° C. (CHCl$_3$).

(c)
2-Ethyl-7-fluoro-10-[4-(3-hydroxypropyl)-1-piperazinyl]-4H-thieno[2,3-b][1,5]benzodiazepine m.p. 145°-148° C. (CH$_2$Cl$_2$/hexane).

(d)
2-Ethyl-10-[4-(2-hydroxyethyl)-1-piperazinyl]-4H-thieno[2,3-b][1,5]benzodiazepine m.p. 175°-176° C. (EtOAc/hexane).

(e)
10-[4-(3-Hydroxypropyl)-1-piperazinyl]-4H-thieno[3,2-b][1,5]benzodiazepine m.p. 172°-173° C. (EtOAc/hexane).

(f)
7-Fluoro-10-[4'-(3-hydroxypropyl)-1'-piperazinyl]-4H-thieno[3,2-b][1,5]benzodiazepine m.p. 138°-140° C. (CHCl$_3$).

(g)
10-[4-(3-hydroxypropyl)-1-piperazinyl]-4H-thieno[3,4-b][1,5]benzodiazepine m.p. 184° C.

EXAMPLE 35

(a)
2-Ethyl-7-fluoro-10-[3-N(4-methyl-1-piperazinyl]-propylamino-4H-thieno[2,3-b][1,5]benzodiazepine 9,10-Dihydro-2-ethyl-7-fluoro-4H-thieno[2,3-b][1,5]benzodiazepin-10-thione (2 g, 0.0072 mol), 1-(3-aminopropyl)-4-phenylpiperazine (1.3 ml), triethylamine (8 ml), and dry dimethylformamide (10 ml) were heated under nitrogen at 65° C. until the reaction was complete by t.l.c. (Et$_2$O) (20 hours). The mixture was poured onto excess molar maleic acid solution, washed twice with ether and basified with 0.88 ammonia solution, extracting with ethylacetate. The combined extracts were washed with water, dried (MgSO$_4$) and the solvent evaporated to give the title product as a yellow semi solid which was crystallised from ethyl acetate/n-hexane, m.p. 181° C.

The following compounds were similarly prepared:

(b)
10-(3-N,N-Dimethylaminopropylamino)-2-ethyl-7-fluoro-4H-thieno[2,3-b][1,5]benzodiazepine dimaleate m.p. 193°-195° C. (isopropanol/n-hexane).

(c)
2-Ethyl-7-fluoro-10-(3-N-morpholinopropylamino)-4H-thieno[2,3-b][1,5]benzodiazepine dimaleate m.p. 182°-186° C. (isopropanol/n-hexane).

(d)
2-Ethyl-7-fluoro-10-(2-hydroxyethylamino)-4H-thieno[2,3-b][1,5]benzodiazepine maleate m.p. 196°-198° C. (ethanol/ethyl acetate/n-hexane).

(e)
10-(2-N,N-Dimethylaminoethylamino)-2-ethyl-7-fluoro-4H-thieno[2,3-b][1,5]benzodiazepine maleate m.p. 183°–184° C. (ethanol/ethyl acetate/n-hexane).

(f)
2-Ethyl-7-fluoro-10-(3-hydroxypropylamino)-4H-thieno[2,3-b][1,5]benzodiazepine maleate m.p. 174°–175° C. (ethanol/ethyl acetate/n-hexane).

(g)
2-Ethyl-7-fluoro-10-(2-N-piperidinoethylamino)-4H-thieno[2,3-b][1,5]benzodiazepine sesquifumarate m.p. 184°–185° C. (ethanol/ethyl acetate/n-hexane).

(h)
2-Ethyl-7-fluoro-10-(2-N-morpholinoethylamino)-4H-thieno[2,3-b][1,5]benzodiazepine fumarate m.p. 189°–203° C. (ethanol/ethyl acetate/n-hexane).

(i)
2-Ethyl-7-fluoro-10-(4-methyl-1-piperazinyl)-4H-thieno[2,3-b][1,5]benzodiazepine m.p. 153°–155° C. (ethylacetate/n-hexane).

(j)
2-Ethyl-7-fluoro-10-(4-phenyl-1-piperazinyl)-4H-thieno[2,3-b][1,5]benzodiazepine m.p. 154°–156° C. ($CH_2Cl_2$/hexane).

(k)
10-(4-Benzyl-1-piperazinyl)-2-ethyl-7-fluoro-4H-thieno[2,3-b][1,5]benzodiazepine m.p. (di HCl salt) 265°–270° C. (EtOH/$Et_2O$).

(l)
10-[4-(m-Chlorophenyl)-1-piperazinyl]-2-ethyl-7-fluoro-4H-thieno[2,3-b][1,5]benzodiazepine hydrochloride m.p. (HCl salt) 250°–260° C.

(m)
2-Ethyl-7-fluoro-10[4-(m-trifluoromethylphenyl)-1-piperazinyl]-4H-thieno[2,3-b][1,5]benzodiazepine hydrochloride m.p. (HCl salt) 184°–187° C.

(n)
10-(2-N-piperidinoethylamino)-4H-thieno[3,4-b][1,5]benzodiazepine m.p. 182°–183° C.

EXAMPLE 36

(a)
10-[4-(3-Decanoyloxypropyl)-1-piperazinyl]-4H-thieno[3,2-b][1,5]benzodiazepine hydrochloride To a solution of 10-[4-(3-hydroxypropyl)-1-piperazinyl]-4H-thieno[3,2-b][1,5]benzodiazepine (1.71 g, 0.005 mol) in dry benzene (40 ml) was added decanoyl chloride (1.42 g, 0.0075 mol) in benzene (10 ml) dropwise with stirring and the solution heated at 75° C. until the reaction had gone to completion by TLC. The reaction mixture on washing gave the title compound.

Similarly, using the process of Example 36(a) other hydroxyalkyl derivatives of Example 34 were esterified to give the corresponding decanoate and enanthate esters.

The following Examples illustrate pharmaceutical formulations containing the active compounds of the invention. The active ingredient used was 2-ethyl-7-fluoro-10-(4-methyl-1-piperazinyl)-4H-thieno[2,3-b][1,5]benzodiazepine; however, it will be appreciated that this compound may be replaced by other active solid compounds of the invention.

EXAMPLE 37

Tablets each containing 10 mg of active ingredient were made up as follows:

| | | |
|---|---|---|
| Active ingredient | 10 | mg |
| Potato Starch | 45 | mg |
| Lactose | 35 | mg |
| Polyvinylpyrrolidone (as 10% solution in water) | 4 | mg |
| Sodium starch glycolate | 4.5 | mg |
| Magnesium Stearate | 0.5 | mg |
| Talc | 1 | mg |
| Total | 100 | mg |

The active ingredient, starch and lactose were passed through a No. 44 mesh B.S. sieve and mixed thoroughly. The solution of polyvinylpyrrolidone was mixed with the resultant powders which were then passed through a No. 12 mesh B.S. sieve. The granules so produced were dried at 50°–60° C. and passed through a No. 16 mesh B.S. sieve. The sodium starch glycolate, magnesium stearate and talc, previously passed through a No. 60 mesh B.S. sieve, were then added to the granules which, after mixing, were compressed on a tablet machine to yield tablets each weighing 100 mg.

EXAMPLE 38

Capsules each containing 20 mg of medicament were made as follows:

| | | |
|---|---|---|
| Active ingredient | 20 | mg |
| Starch | 89 | mg |
| Lactose | 89 | mg |
| Magnesium Stearate | 2 | mg |
| Total | 200 | mg |

The active ingredient, lactose, starch and magnesium stearate were passed through a No. 44 mesh B.S. sieve and filled into hard gelatin capsules in 200 mg quantities.

EXAMPLE 39

Suppositories each containing 25 mg of active ingredient were made as follows:

| | |
|---|---|
| Medicament | 25 mg |
| Saturated fatty acid glycerides to | 2,000 mg |

The active ingredient was passed through a No. 60 mesh B.S. sieve and suspended in the saturated fatty acid glycerides previously melted using the minimum heat necessary. The mixture was then poured into a suppository mould of nominal 2 g capacity and allowed to cool.

EXAMPLE 40

Suspensions each containing 5 mg of medicament per 5 ml dose were made as follows:

| Medicament | 5 | mg |
|---|---|---|
| Sodium carboxymethyl-cellulose 50 | 50 | mg |
| Syrup | 1.25 | ml |
| Benzoic Acid solution | 0.10 | ml |
| Flavour | q.s. | |
| Colour | q.s. | |
| Chloroform water to | 5 | ml |

The medicament was passed through a No. 44 mesh B.S. sieve and mixed with the sodium carboxymethyl-cellulose 50 and syrup to form a smooth paste. The benzoic acid solution, flavour and colour were diluted with some of the chloroform water and added, with constant stirring. Sufficient chloroform water was then added to produce the required volume.

We claim:

1. A thieno[3,2-b][1,5]benzodiazepine of the formula

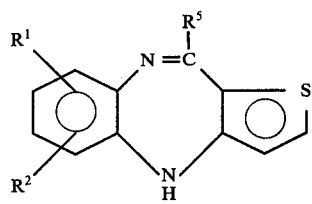

or an acid addition salt thereof, wherein $R^1$ and $R^2$ independently represent hydrogen, $C_{1-4}$ alkyl, halogen, $C_{1-4}$ haloalkyl, nitro, amino, $C_{1-4}$ alkoxy, $C_{1-4}$ alkylthio or a group of the formula $-SO_2N(R^4)_2$ where $R^4$ is $C_{1-4}$ alkyl; wherein $R^5$ is a group of the formula

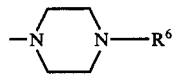

wherein $R^6$ is hydrogen, phenyl, halo phenyl, $C_{1-4}$ alkyl, $C_{1-4}$ carbalkoxy or $-(CH_2)_nOH$ where $n$ is 2 or 3; and wherein the thiophene ring is unsubstituted or is substituted by a $C_{1-4}$ alkyl group.

2. A thieno[3,2-b][1,5]benzodiazepine of claim 1 wherein $R^1$ and $R^2$ are optional substituents at the 6- or 7-positions of the thieno[1,5]benzodiazepine system.

3. A thieno[3,2-b][1,5]benzodiazepine of claim 1, wherein $R^1$ is a 6- or 7-halo or trifluoromethyl substituent when $R^2$ is hydrogen.

4. A thieno[3,2-b][1,5]benzodiazepine of claim 1 wherein $R^6$ is methyl.

5. An acid addition salt according to claim 1 which is pharmaceutically-acceptable.

6. A pharmaceutical formulation according to claim 7 in the form of a capsule, tablet or injection solution.

7. A pharmaceutical formulation comprising as an active ingredient a chemotherapeutically effective amount of a compound of the formula:

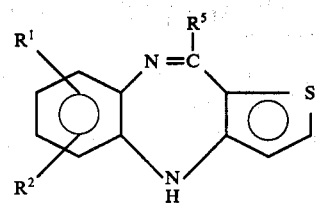

or a pharmaceutically-acceptable salt thereof, wherein $R^1$ and $R^2$ independently represent hydrogen, $C_{1-4}$ alkyl, halogen, $C_{1-4}$ haloalkyl, nitro, amino, $C_{1-4}$ alkoxy, $C_{1-4}$ alkylthio or a group of the formula $-SO_2N(R^4)_2$ where $R^4$ is $C_{1-4}$ alkyl; wherein $R^5$ is a group of the formula:

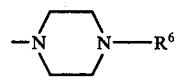

wherein $R^6$ is hydrogen, phenyl, halo phenyl, $C_{1-4}$ alkyl, $C_{1-4}$ carbalkoxy or $-(CH_2)_nOH$ where $n$ is 2 or 3; and wherein the thiophene ring is unsubstituted or is substituted by a $C_{1-4}$ alkyl group.

8. A method of treating an animal suffering from, or susceptible to, disorders of the CNS, which comprises administering to the animal a chemotherapeutically effective amount of a compound of the formula:

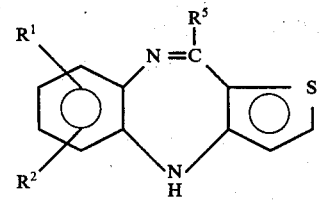

or a pharmaceutically-acceptable salt thereof, wherein $R^1$ and $R^2$ independently represent hydrogen, $C_{1-4}$ alkyl, halogen, $C_{1-4}$ haloalkyl, nitro, amino, $C_{1-4}$ alkoxy, $C_{1-4}$ alkylthio or a group of the formula $-SO_2N(R^4)_2$ where $R^4$ is $C_{1-4}$ alkyl; wherein $R^5$ is a group of the formula:

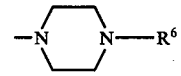

wherein $R^6$ is hydrogen, phenyl, halo phenyl, $C_{1-4}$ alkyl, $C_{1-4}$ carbalkoxy or $-(CH_2)_nOH$ where $n$ is 2 or 3; and wherein the thiophene ring is unsubstituted or is substituted by a $C_{1-4}$ alkyl group.

9. The compound of claim 1 which is 7-fluoro-10-(4-methyl-1-piperazinyl)-4H-thieno[3,2-b][1,5]benzodiazepine or a pharmaceutically-acceptable salt thereof.

* * * * *